United States Patent [19]

Terman et al.

[11] Patent Number: 4,699,783

[45] Date of Patent: Oct. 13, 1987

[54] PRODUCTS AND METHODS FOR TREATMENT OF CANCER

[76] Inventors: David S. Terman, 25371 Outlook Dr., Carmel, Calif. 93923; Joseph P. Balint, 169 Crooks Ave., Clifton, N.J. 07011; John J. Langone, 7735 Candlegreen, Houston, Tex. 77071

[21] Appl. No.: 542,239

[22] Filed: Oct. 14, 1983

Related U.S. Application Data

[63] Continuation-in-part of Ser. No. 472,362, Mar. 11, 1983, abandoned, which is a continuation-in-part of Ser. No. 366,436, Apr. 7, 1982, abandoned.

[51] Int. Cl.$^4$ ............................................ A61K 39/395
[52] U.S. Cl. ...................................... 424/85; 424/101; 530/387
[58] Field of Search ............. 424/85, 101; 260/112 R, 260/112 B; 530/387

[56] References Cited

PUBLICATIONS

Terman, D. et al., Science, vol. 209, pp. 1237–1239, 1980.
Terman, D. et al., J. Immunology, vol. 124, pp. 795–805, 1980.
Terman, D. et al., The New England Journal of Medicine, vol. 305, pp. 1195–1200, 1981.

*Primary Examiner*—Blondel Hazel
*Attorney, Agent, or Firm*—Fulbright & Jaworski

[57] ABSTRACT

Disclosed are compositions for the treatment of cancer, such as lymphomas and solid tumors, methods of producing these compositions, and methods and regimens in using these compositions in the treatment of hosts having cancer. The compositions are (1) tumor immune preparations which can be prepared by acidification or alkalinization of an enriched immunoglobulin effluent from forced flow electrophoresis of plasma from a normal or a tumor bearing host, (2) tumor immune globulin which can be prepared by acidifying a Cohn gamma globulin fraction from a normal or a tumor bearing host, (3) protein A-IgG preparations which can be prepared by perfusion of plasma over protein A from *staphylococcus aureus* Cowans I and precipitating the complex or by incubating protein A and purified IgG or IgG in plasma, (4) tumor immune plasma preparations which may be prepared by acidification of plasma from normal or tumor bearing hosts, and (5) zymosan activated plasma which can be prepared by incubating plasma with zymosan and then removing the zymosan. Infusing of the compositions alone or in combination with each other and with various chemotherapeutic agents has resulted in tumoricidal reactions, objective anti-tumor effects, and sustained tumor regressions.

8 Claims, 7 Drawing Figures

POLYACRYLAMIDE GEL ELECTROPHERSIS (PAGE) OF HIGH MOLECULAR WEIGHT IgG ISOLATED FROM SERUM AFTER PERFUSION OVER PROTEIN A COLLODION CHARCOAL.

PAGE PROFILE OF PROTEIN A ISOLATED FROM SERUM AFTER PERFUSION OVER PROTEIN A COLLODION CHARCOAL.

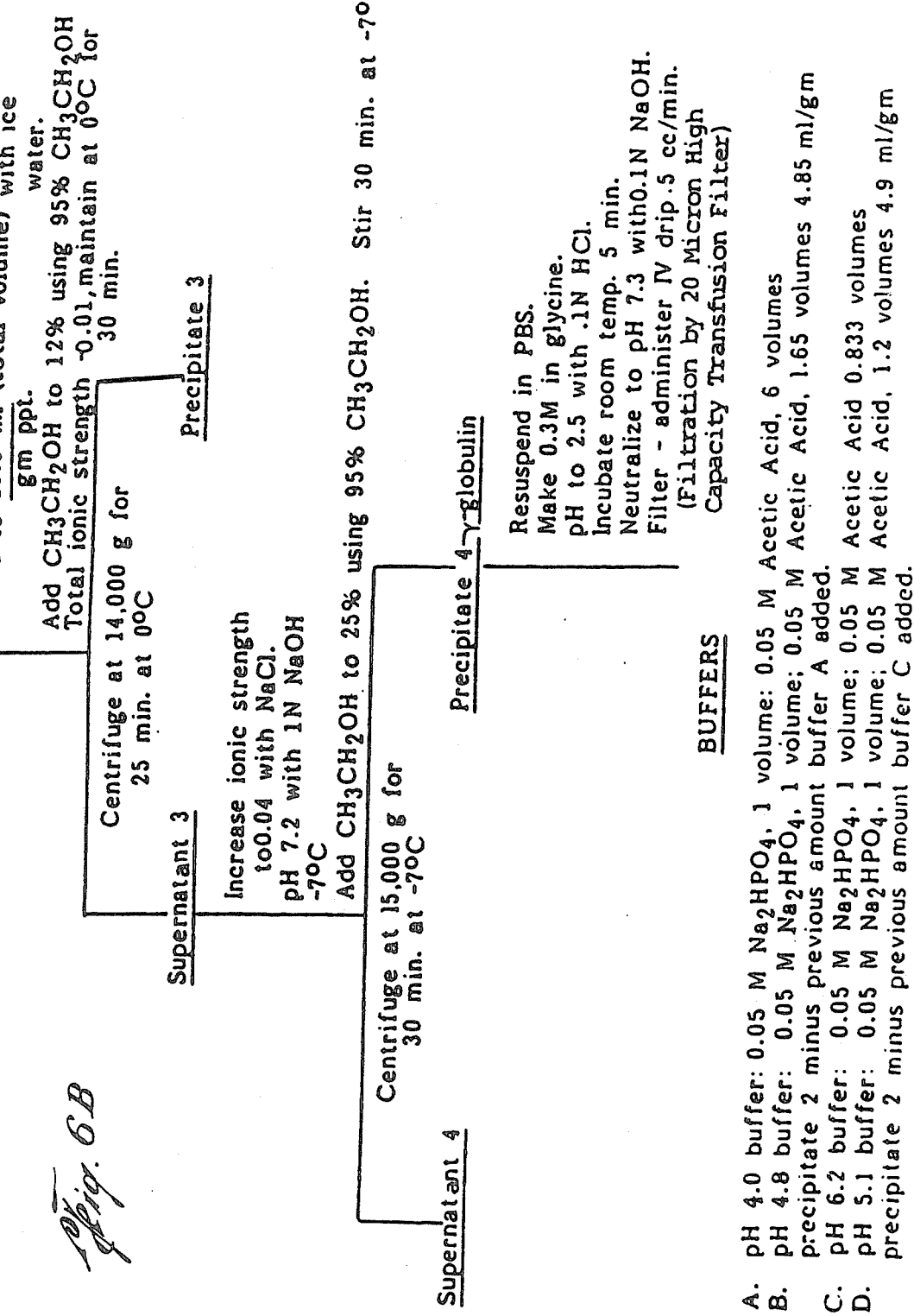

PRODUCTS AND METHODS FOR TREATMENT OF CANCER

BACKGROUND OF INVENTIONS

CROSS REFERENCE TO RELATED APPLICATION

The present invention is a continuation-in-part of application Ser. No. 472,362 filed Mar. 11, 1983 now abandoned, which is a continuation-in-part of application Ser. No. 366,436 filed Apr. 7, 1982 now abandoned.

FIELD OF INVENTION

The present invention relates to immunotherapy and chemotherapy products and methods for treatment of hosts having cancer.

PRIOR ART - IMMUNOTHERAPY

A. Forced Flow Electrophoresis

Forced flow electrophoresis is a technique whereby a gamma globulin rich fraction is electrophoretically separated from heparinized whole blood maintained in an extracorporeal circulation (1-5). The general procedure is similar to that employed with artificial kidneys and more specifically with blood electrodialysis (6). Forced flow electrophoresis (FFE) was initially conceived as a large scale electrophoretic technique for rapid fractionation of biological materials permitting the purification of isoelectric protein components (5). The principles of function of the forced flow electrophoresis are as follows: at neutral pH all plasma proteins with the exception of gamma globulin will migrate into an electric field. This principle is used to reclaim all plasma proteins and to separate gamma globulin. It has proven to be a more versatile tool, suitable for the study of a variety of electrokinetic membrane phenomena such as electrofiltration and its application to water purification (7), electroadsorption of bacteriophages (8), blood electrodialysis and the electroosmotic concentration and/or desalting of protein solutions (9). FFE may be designed for on-line operation and has been used to remove immunoglobulins from dogs to prevent or delay kidney xenograft rejection (10). The use of this device in treatment of hosts with cancer has not to the inventor's knowledge been done before.

In the course of FFE an effluent (EIE) is collected which is rich in gamma globulin but contains other plasma proteins as well (10). Prior to the present invention, this effluent has been discarded without further treatment. The present invention addresses itself to the collection of this effluent with the FFE device, its subsequent treatment and readministration to the host with cancer.

B. Protein A IgG Complexes

Protein A is a constituent of the cell wall of staphylococcus aureus Cowans I which reacts with the Fc fragments of immunoglobulins from many mammalian species to form immune complexes, which immune complexes fix complement and consume complement components (11-16). In previous studies on dogs with spontaneous mammary adenocarcinoma, an excellent model of human breast cancer, plasma was circulated over protein A bearing staphylococcus (SpA) which was immobilized in a microporous membrane filtration system and placed on line with plasma emerging from a continuous flow plasma cell separator (17). Shortly after circulation of one plasma volume over protein A bearing staphylococcus, tumor necrosis followed by objective tumor regressions were observed. These effects were not seen when plasma was circulated over protein A deficient staphylococcus (17). The findings of tumor regressions in this experimental canine system were confirmed in an independent study (18). Plasma perfusion was then refined and similar tumor necrolytic responses were observed after plasma perfusion over purified protein A which was immobilized in a collodion charcoal matrix (protein A collodion charcoal, PACC) (19).

This form of therapy was applied to 5 consecutive human patients with breast adenocarcinoma and acute tumoricidal reactions were noted shortly after perfusions over PACC. After repeated treatments, objective tumor regressive effects were observed in 4 of these patients (20).

Prior studies in dogs and man with spontaneous breast adenocarcinoma showed (among other things) the following results when the subject was treated with plasma which had been perfused over immobilized SpA or PACC (17, 19, 20): The rapid onset of acute pain and visible morphologic changes in chest wall tumors after extracorporeal perfusion of small volumes of plasma over PACC suggested that these effects were produced by factors generated in plasma after passage over PACC (17, 19, 20). The procedure was technically simplified by eliminating the on-line extracorporeal circulation system and instead small aliquots of autologous or homologous plasma, previously collected by phlebotomy, were passaged over PACC off-line followed by direct infusion into patients (20). Patients treated entirely with the off-line plasma perfusion showed acute pain with similar morphologic responses and tumor regressive effects to those observed with the on-line extracorporeal system (20). Moreover, the tumoricidal responses in both dogs and man were accompanied by serologic and immunohistochemical changes, namely increased solid phase C1q binding and C5a levels and decline in C3 associated with deposits of IgG and C3 on tumor cell membranes (17, 20, 21).

SpA has the ability to bind to the Fc region of IgG which not only can result in complement activation and other effects in vitro but also can produce effects in vivo that resemble immune reactions brought about by antigen-antibody complexes. Some of them appear to involve complement activated by SpA-IgG complexes in solution. For example, SpA administered intradermally to normal human subjects in doses as low as 10 ug produced wheal and erythema reactions detected after 30 minutes and a later reaction with maximum intensity after 24 to 48 hours. Similarly, as little as 10 ug SpA given intradermally to guinea pigs resulted in a significant arthus-like reaction and 300-400 ug gave a hemorrhagic reaction with maximum intensity of 12 to 24 hours (22). Guinea pigs given 500 to 1000 ug intracardiac suffered fatal anaphylactic shock that could be prevented by prior administration of antihistamines. Heczko, et al (23) also found that guinea pigs sensitized with as little as 50 ug SpA in complete Freunds adjuvant gave a delayed reaction that was maximal at 24 hours, whereas the same dose given in in complete adjuvant or in saline gave an arthus reaction that was maximal at 6 hours. In contrast to man and guinea pig, other species with IgG that does not precipitate SpA failed to give hypersensitivity reactions when given SpA alone. Thus rabbits given the single injection of up to 6 mg SpA and mice given from 10 to 500 ug showed neither early onset nor delayed reactions (24, 25). However, in rabbits a direct arthus reaction was produced in 5 to 10 hours by administration of 100 to 180 mg human IgG intravenously followed in 10 to 15 minutes by 0.025-21.5 mg SpA intradermally and hemorrhagic necrosis was evident 18 to 24 hours after intradermal injections of preformed precipitates between human IgG and SpA (24). Soluble complexes between rabbit IgG and $125_I$ SpA were cleared rapidly from the circulation of rabbits by liver and spleen and up to 49% of label complexes were taken up in vitro by saline perfused rabbit liver during one passage (25).

It is known that SpA added to human, guinea pig, rabbit or pig serum causes weak and marked depletion of complement activity depending on the species (26-29). Mixtures of SpA and human normal or myeloma IgG or Fc fragments or normal guinea pig IgG aggregated by SpA had a similar effect (30, 31). Complexes between SpA and both guinea pig subclasses $IgG_1$ and $IgG_2$ fixed complement, whereas antigen-antibody complexes involving $IgG_3$ did not (30, 31). When SpA was added to whole human sera titers of the 9 components of complement except for C7 which was not determined, decreased from 30% (C8) to 85% (C3) and optimal inhibition occurred in IgG excess. Preformed complexes between SpA and the Fc fragment of a complement fixing myeloma $IgG_1$ prepared under conditions for maximum activity decreased the whole complement titer by 64% and the titers of the individual components from 4% to 99% (C3) (14). SpA also inhibited binding of C1 to either heat aggregated IgG or to the IgG myeloma 1 protein but had no effect on the binding of C1 to IgG (14). Depletion of complement activity depended on the amount of SpA relative to IgG. Thus, as the dose of SpA serum increased, there was a maximum level of complement activation which decreased at high SpA concentrations (14, 26, 28). This effect was interpreted to mean that high concentrations of SpA were inhibiting C1 binding. Experiments of Langone, et al (32, 33, 34) clarified the effect of SpA on antibody activity. Complexes between IgG and SpA formed at relatively high or low doses of SpA behave like authentic IgG. SpA-IgG complexes prepared with the empirical formula $[(IgG)_2 SpA]_n$ behave like IgM in their hemolytic capability and in the way they interact with whole complement or purified C1 (34). By fluorescence quenching and light scattering techniques, rabbit Fc was shown to have two binding sites for monovalent fragment B and that complexes were formed with two to four molecules of Fc fragments bridged by SpA (35). Moreover, complex formation between IgG and SpA enhances antibody affinities significantly probably owing to multipoint attachment (13).

Human polymorphonuclear leukocytes rapidly ingest and degrade insoluble complexes prepared with human IgG and SpA (36, 37) white blood cells release histamine in the presence of SpA (38). The degree of phagocytosis is dependent on the dose of SpA and was optimal depending on the precipitates formed, and the equivalent release of myeloperoxidase correlated with phagocytosis of complexes. $125_I$ labeled IgG was used to show that uptake depended on the concentration of neutrophils, the nature of the complexes, the incubation time, and the presence of serum factors (36).

The present invention shows that protein A-IgG complexes are formed after plasma perfusion over PACC. Similar complexes prepared by incubating protein A with IgG or serum in various molar ratios and then given intravenously to tumor bearing hosts has resulted in tumoricidal reactions and tumor regressions. This represents a new product for use in treatment of cancer.

C. Acidification And Alkalinization

It has been recognized for many years that subjecting antigen-antibody complexes whether they be naturally occurring or artificially prepared to extremes of pH on either acid or alkaline side will result in essentially their complete dissociation into their respective components. Subjecting artificially prepared complexes of bovine serum albumin-antibovine serum albumin to acid pH results in dissociation into their respective components as first demonstrated by Campbell, et al (39). This concept has been employed in the field of immunology for the isolation of antigens and antibodies that are present in the form of an immune complex. The method of dissociation of antibodies from antigen-antibody complexes by acidification and antibody isolation after antigen removal by ultrafiltration at low pH was described by Sjogren, et al (40) in a mouse tumor system. More recently, potentially cytotoxic antibodies directed to leukemia-associated antigens were found in serum during the acute stage of acute myelogenous leukemia. After ultrafiltration at low pH significant complement dependent cytotoxicity was detectable in most of the sera tested (41). In addition, Dorsett, et al, (42) isolated tumor specific antibodies from ovarian effusions of ovarian carcinomas by means of salt precipitation and then incubation at pH 2.8 followed by neutralization of the samples by slow addition to sodium hydroxide. Antibodies liberated were tested by indirect immunofluorescence and showed substantial increase in titer. The concept of alkalinization of solutions to dissociate immune complexes was initially described by Kabat and Mayer (43) and has been used for this purpose for many years.

The acidification or alkalinization of forced flow electrophoresis effluent or tumor bearing plasma and its use in the treatment of cancer as will be described herein has not, to the inventor's knowledge, been previously accomplished or reported.

D. Tumor Immune Globulin

Immunoglobulin use in clinical medicine began with the use of antitoxins by Behring and Kitasato (44) and progressed to the clinical use of animal antitoxins in the prophylaxis of human disease. The use of human immunoglobulin preparations for passive immunization began with the studies of McKhann and co-workers (45, 46) who used ammonium sulfate to isolate globulin fractions from placental extracts. In 1936, these fractions, which proved to be effective in the prevention or modification of measles, were referred to as immune globulin (human) (47). The major advance in the field came with the exploitation of cold ethanol for the fractionation of immunoglobulins from human plasma and the demonstration that fraction II i.e. immune serum globulin was effective for the prophylaxis of measles (48, 49) and hepatitis (50, 51) as well as for the treatment of immunodeficiency (47). The development of immunoglobulin use in the United States has consisted largely of the introduction of specific immune globulins. Products such as tetanus immune globulin, anti-D globulin, and immune globulin in rabies endure relatively secure status in clinical medicine. The newest of these products is hepatitis B immune globulin and still others such as varicella-zoster immune globulin remain under investigation. Preparations exist now for intravenous use of gamma globulin which include the reduced and alkylated, the salt fractionated, Beta propiolactone treated and the pH 4 treated preparations (52–57). These preparations have shown efficacy and all have shown a wide variety of side effects. The side effects appear to be substantially reduced with pH 4 preparation and an indication existed that side effects could be avoided by slow infusion. Ideal properties of gamma globulin include the lack of fragmentation, the lack of both aggregation and IgA, and stability of the preparation. It should be adequate for use either intramuscularly or intravenously and have no hepatitis risk.

The use of tumor specific antibodies for specific active immunotherapy has taken the following courses. Trials with xenogeneic sera have been performed and require the administration of foreign protein for a prolonged period with resultant risk of allergic reactions. Nevertheless, in an early trial, Lindstrom had some clinical response upon administration of sera prepared in rabbits after immunization with myeloid leukemia cells (58). DeCarvalho prepared hyperimmune gamma globulin in horses against antigens separated from normal antigens in tumor tissue by precipitation of the latter by antibodies against normal tissues. Thirteen of 15 leukemia patients had remissions lasting from 4 weeks to 29 months on immune serum globulin (59). Sekla and colleagues were unable to produce remission in 5 patients with heterologous immune globulins prepared in a slightly different fashion (60). Tsirimbas, et al treated 5 patients having chronic lymphatic leukemia with horse anti-lymphocyte serum. In 3 of 5 patients the peripheral cell counts fell to approximately 40% of their initial value (61). DeCarvalho saw objective evidences of response in solid tumor patients with globulins prepared as for the leukemias (59). Marsh, et al administered a rabbit anti-tumor serum to patients with a variety of solid tumors (62). They saw no clinical effect although at autopsy antibody was selectively localized in areas of sarcoma cells. In a recent trial using serum prepared from melanoma-immunized chimpanzees, the investigators noted acute necrosis of visceral disease in 2 of 3 patients although the regressions were incomplete and complicated by fatal thrombocytopenia in 1 patient (63).

Allogeneic sera have been studied for their therapeutic effect in leukemia as well. Several investigators have attempted to treat leukemias and lymphomas with serums containing antibodies against human lymphocytes. In a study by Laslow, et al (64) anti-lymphocyte plasma was prepared by immunizing normal subjects against normal lymphocytes. IgG was then separated from this plasma and administered to 3 patients with chronic lymphocytic leukemia. In each patient there was a transient lymphopenia and decrease in lymph node size after infusion. Djarassi treated 4 patients with acute lymphocytic leukemia with serum from a patient with thalassemia major who had been sensitized against both granulocytes and lymphocytes of many individuals. In all 4 patients, there was a fall in peripheral white count (65). Herberman administered serum with cytotoxic antibodies from a multi-gravid female to 7 patients with lymphoproliferative disorders. His patients responded with falls in lymphocyte and platelet counts averaging 48.8% to 25.5% of pre-treatment values which lasted one day. Two of the five patients had shrinkage of peripheral lymphatic tissue, 4 patients had minor side effects such as fever and chills, and 2 had respiratory distress (66). Allogeneic sera in which the donors had been purposely immunized against tumor cells have also been studied. Brittingham and Chaplin immunized a normal donor with leukocytes from a patient with chronic myelocytic leukemia. The normal subject was then reimmunized three years later with whole blood from a second patient with chronic myelocytic leukemia. Antileukocyte antibody active against donor cells appeared in the normal subject. Gamma globulin was obtained from this donor and this donor's plasma was administered to the leukemic patients whose cells had been used for reimmunization. There was no apparent beneficial effect on the patient's illness (67). Skirkovich and co-workers immunized patients with leukemia cells from other patients. Eight to 15 days after immunization, plasma was exchanged 2 to 3 times between donor pairs of the patients. Six pairs of children were treated and 3 complete and 5 partial hematologic remissions were observed. Seven of these responding patients had received steroid and cytostatic therapy as well but one complete remission was achieved with immunotherapy alone (68). Remission plasma has also been given for passive therapy. Skirkovich and co-workers collected autologous plasma and leukocytes early in remission and administered these to patients in later stages of remission. They felt that remission duration was prolonged by this maneuver (69). Ngu using late remission sera from patients with Burkitts lymphoma produced regressions in patients with active diseases (70). Serum from patients with regression of malignant melanoma has occasionally induced regression when administered to other patients.

Investigators have attempted to exploit the specificity of antibody to deliver other cytotoxic materials directly to the tumor cell in animal models. Chlorambucil and daunomycin have been bound to anti-tumor antibodies (72, 73) and antibodies have also been labeled with radioactive isotopes such as $131_I$ (74). They have also been conjugated to toxins such as diptheria (75) and enzymes with cytotoxic potential (76). A possible synergistic effect between antibody and chemotherapy has been described by Segerling, et al and shows that guinea pig hepatoma cells normally resistant to killing by antibody and complement are rendered sensitive after treatment with chemotherapeutic agents (77).

While it is apparent that much work has been done in the prior art regarding the administration of immune globulin preparations to tumor-bearing animals and humans, the results of these experiments have been mixed. Initially, it should be remarked that these treatments have not been consistently effective to treat the tumor. A variety of types of treatments have been employed, ranging from the use of the patient's own serum through the use of serum from other patients having similar diseases and going as far as the use of sera from animals of different species. More recently, attempts have been made to treat patients using nonoclonal antibodies generated in mice to the specific tumor possessed by the patient. These various efforts are evidence of the general lack of success in the prior art techniques, as disclosed in the publications mentioned above. In contrast to the mixed results obtained in the prior art, the tumor associated immune globulin preparation of the present invention is able to produce consistent tumoricidal activity when injected into tumor-bearing hosts, both human and animal. Moreover, the sourcing of this material involves significantly fewer complications than in the prior art, since any immune globulin obtained from any member of the species can be used, which material can readily be obtained by (for example) plasmapherising hosts having immune complexes containing the desired antibody or obtaining the antibody from Cohn fractionation of the plasma obtained from said host. The techniques disclosed herein allow preparation of a much more abundant source of generally effective anti-tumor reagent than could possibly have been prepared by the techniques of the prior art.

Herein, we describe a new tumor immune globulin obtained from serum of tumor bearing hosts as well as a method for producing it. This substance shows tumoricidal effects when administered to hosts with cancer.

E. Complement Activation

The human complement system consists of a diverse assortment of plasma proteins. More than 20 components in all participate in orderly reaction sequences that eventually result in complement activation. Accumulated evidence supports the contention that the complement system serves as a fundamental element of normal host defense mechanisms and as a consequence complement activation is commonly associated with a variety of pathological states (78, 79, 80). There are two primary modes termed the classical and alternative pathways whereby complement is activated. These two pathways may be generally distinguished according to the process by which initiation occurs. Regardless of the mode of complement activation it is the conversion of the pivotal C3 component into a C3a and C3b fragments that signals the hallmark event of activation. A C3 convertase is formed as a result of activation of the classical or alternative pathway. C3 conversion gives rise to the formation of an enzyme complex (C5 convertase) which then in turn cleaves C5 to yield the fragments C5a and C5b. C5a is subsequently released into solution while the C5b portion of the molecule plays an essential role in initiating the formation of the lytic membrane attack complex.

C3a and C5a are molecules termed anaphylatoxins and are extremely potent bioactive substances that play a key role as mediators in the acute inflammatory response (81, 82). Both C3a and C5a share certain spasmogenic properties with C3a being effective in the nanomolar concentration range and C5a in the sub-nanomolar concentration range (83). Both factors have been shown to increase vascular permeability (84, 85) as well as to induce release of histamine from mast cells (86). C5a is a chemotactic factor and this glycopolypeptide appears to be a major mediator of neutrophil induced inflammation (87). Several mechanisms are considered effective in limiting the biological activity of anaphylatoxins. A serum exopeptidase efficiently removes an essential C terminal arginyl residue from the anaphylatoxin molecules and renders both C3a and C5a virtually incapable of spasmogenic action within seconds of their being released into the circulation (88). The product C5a des Arg nonetheless retains an ability to promote chemotaxis (89).

C3a is a single chain polypiptide of 77 amino acid residues and has a molecular weight of 9000. Human C5a anaphylatoxin is a single chain glycopeptide of 74 amino acid residues containing a single oligosaccharide unit attached to the asparagine residue in position 64. The combined molecular weight of the polypeptide and oligosaccharide moiety is 11,000 (90, 91).

In previous studies in humans, it was observed that serum levels of C5a (and congeners) were elevated shortly after plasma perfusion over protein A collodion charcoal (21). The appearance of C5a was associated with peripheral vasodilatation and appearance of interstitial fluid (20, 21). In one instance, there was evidence of pulmonary congestion at the time C5a was detected (21). Moreover, it was observed that acute tumoricidal reactions in these patients were associated with the appearance of fluid filled vesicles over cutaneous tumor sites containing polymorphonuclear leukocytes (20). Since C5a is known to produce an increase in vascular permeability and vasodilatation and is chemotactic for neutrophils, it might be contributing to the observed physiologic effects after protein A perfusion and perhaps, improve the ingress of circulating tumoricidal factors into tumorous sites.

Kassel, et al have shown that the administration of pure C5 in particular to leukemic mice resulted in significant leukemic regressions (92). AKR mice with spontaneous leukemia were infused with normal serum from a variety of species. Leukemia cell destruction was produced by serum from strains of mice possessing the full spectrum of complement components but not by serum from murine strains with genetically determined deficiency of C5. Serum from guinea pigs, horses and humans also caused destruction of leukemia cells. The projected mechanisms by which C5 produced leukemia cell destruction in AKR mice are the following: (a) C5 may have a direct effect on leukemia cells by providing a missing complement link which allows cytotoxic antibodies produced by the host to induce cell lysis, (b) C5 reacts at a site other than leukemia cell surfaces e.g. with antigen-antibody complexes in the blood or kidney thus causing the release of lymphokines which themselves mediate leukemia cell destruction, (c) the antileukemic effect of C5 is independent of pre-existing immune response suggesting another mechanism for specific killing of leukemia cells.

SUMMARY

The present invention provides tumor-associated immune globulin preparations which are useful either by themselves or in combination with other modalities for the treatment of cancer. It is the essence of one aspect of the present invention that the immune globulins in plasma from the subject to be treated or from other tumor-bearing animals of the same species (including humans) may be treated so as to:

(a) dissociate the circulating immune globulins from the circulating soluble tumor antigens with which they are complexed; and (b) aggregate these freed immune globulins to produce a material having augmented tumoricidal activity when injected into the tumor-bearing host.

It should be noted that this dissociation step may be accomplished by any of a number of known dissociative techniques, including a substantial variation in pH from that normally experienced in the serum, a large change in the ionic strength (as by addition of salts), heating, or the like, provided that the dissociative technique used must be sufficient to separate the circulating immune complexes into the desired immune globulin and the soluble tumor-specific antigen without substantially denaturing the desired immune globulin.

One preferred technique which has been employed to effect this dissociation is the treatment of the obtained immune complex with acid or base under dissociating conditions for a sufficient time to effectively dissociate the complexes. As is recognized in the art, a pH in the range of from about 3.2 to 1.5 is generally sufficient to cause this dissociation. Time ranges which would be expected to be effective for this dissociation go from approximately two minutes up to as long as eight hours or longer if desired. The present inventor has found that treatment with acid to lower the pH to approximately 2.5 for about five minutes, followed by a rapid neutralization to approximately pH 7.4 is effective to produce the desired material. If an alternate dissociative technique is employed, it may be necessary to subsequently treat the material to cause the desired aggregation of the immune globulin; however, if the acid treatment is used, the aggregation occurs substantially simultaneously during treatment.

As a further aspect of the present invention, we disclose various complexes between immune globulins and Protein A. These complexes may be between Protein A and immune globulin from either tumor-bearing hosts or normals. These complexes may be prepared most simply by mixing Protein A with serum from a selected human or animal tumor-bearing host or normal, but these may also be prepared by passaging serum through a column having either Protein A or Protein A bearing staphylococcus attached to the solid phase thereof. Additionally, these complexes may be prepared by combining Protein A with purified IgG preparations obtained from serum of either tumor-bearing hosts or normals. These purified immunoglobulin preparations may be obtained by (for example) Cohn fractionation, electrophoresis, or other methods discussed in this disclosure or known to one of skill in the art.

These Protein A-immune globulin complexes may be prepared in a wide range of effective ratios of Protein A to immune globulin, the only criterion being that the complex be effective in the treatment of tumors. These ratios may range from 1:1000 Protein A/globulin up to 1:2 Protein A/globulin. Ratios of approximately 1 to 100 have been found to be particularly effective. These complexes may be obtained conveniently by precipitation as is known in the art. A useful precipitation technique is by use of such materials known to those skilled in the art. These immune globulins could, of course, be monoclonal antibodies generated in mice or other animals to the exact tumor possessed by the host or to the same sort of tumor in other members in the same species of animals.

Further aspects of the present invention are the following products useful in the treatment of hosts having cancer:

Product 1: A tumor associated immunoglobulin preparation having tumorcidal potentiating activity, and derived from plasma of a normal or tumor-bearing host, which preparation comprises predominantly IgG and IgM and which has titers of tumor associated antibodies at least double that of EIE from said host and Clq-binding in fractions sedimenting beyond 7S on sucrose density gradient analysis. By the term "tumor associated" is intended immunoglobulins which react with an antigen that is related or associated to a tumor but which also may be found in other normal body tissues. It is recognized at the moment that these tumor associated immunoglobulins are useful for detection or treatment of tumors even though they are not completely specific for the tumor alone. This tumor associated immunoglobulin preparation may conveniently be prepared from the enriched immunoglobulin effluent (EIE) obtained from forced flow electrophoresis of plasma of the said host by subjecting the same to either a substantial increase or a substantial lowering in pH compared to that of normal plasma for an effective dissociating period of time as described in detail elsewhere in this application. The material so prepared, when compared to untreated EIE, shows reduced levels of IgG, IgM, and immune complexes, but increased titers of tumor associated antibodies and increased Clq binding in heavy sedimenting fractions.

Product 2: A tumor associated immunoglobulin preparation having tumoricidal potentiating activity and derived from plasma of a normal or tumor-bearing host, which preparation comprises IgG with small amounts of IgA, substantially free of IgM and complement, which has a titer of tumor associated antibody at least 1.5 times that of a Cohn gamma globulin fraction from said host and which demonstrates increased Clq binding IgG in fractions sedimenting beyond 7S on sucrose density gradient analysis and which has minimal anti-complementary activity. When administered to hosts having tumors, and particularly tumors of a similar histologic type as the tumor in the host from which the antibody is derived, the preparation induces tumoricidal reaction. It should be understood that the term "tumoricidal reaotion" as used herein means that the material under discussion promotes or assists in the killing of tumor cells. One method of preparing this Product 2 is to obtain the gamma globulin fraction from the plasma of a human or animal by Cohn fractionation or one of its known variants. Once this material has been obtained, it is then treated as previously described above by a dissociating technique such as acidification followed by rapid neutralization. Compared to the untreated gamma globulin Cohn fraction, the tumor associated immune globulin preparation described herein has lower levels of IgG and IgA, increased Clq binding in heavy sedimenting fractions, increased levels of tumor associated antibody, and less anti-complementary activity.

Product 3: Protein A-IgG preparation with the following properties:

(a) comprises predominately IgG heavy and light chains and protein A by polyacrylamide gel electrophoresis.

(b) is identified in fractions sedimenting beyond 7S on sucrose density gradient with increased Clq binding activity.

(c) dissociates into lower molecular weight Clq binding fragments under acid conditions.

(d) is precipitable with 5% polyethylene glycol.

(e) shows anti-complementary activity.

(f) inhibits Fc dependent lymphocyte rosette formation.

(g) induce neutrophils to release myeloperoxidase, cathepsins and superoxide anions.

(h) induces hemagglutination of canine erythrocytes.

(i) induces non-specific complement depletion.

(j) is generated in normal and tumor bearing serum after perfusion over protein A collodion charcoal columns by complement independent mechanism and is not present in pretreatment serum.

If specific antibody containing serum is perfused over protein A collodion charcoal, the protein A-IgG complexes in post perfusion serum retain the properties shown above, (a) through (j), but acquire unique properties as given below:

These preparations have been found to have tumor associated antibody activity in the PEG precipitable fraction. When protein-IgG preparation is infused into a tumor-bearing host at a tumoricidally effective concentration, tumoricidal reactions and tumor regression are observed. Specific antibodies in the PEG precipitable fraction have been found in sera of dogs immunized with human breast carcinoma (MCF-7), and with human erythrocytes. This latter experiment is used as a model system for studying antibody reactions, even though the antigen being used is not a tumor antigen.

We have found that the protein A used in preparing the protein A-IgG conjugates contains staphylococcal enterotoxins. Sodium dedecylsulfate polyacrylamide gel electrophoresis (SDS-PAGE) analysis of the protein A lot used in our clinical trials showed in addition to the protein A band, two distinct bands at 22,000 and 28,000 m.w. respectively. One of the bands comigrated with staphylococcal enterotoxin A. SDS-radio-PAGE confirmed the presence of two peaks at approximately 22,000 and 28,000 m.w. We began a systematic search for enterotoxins in Pharmacia protein A preparations and developed competitive inhibition radioimmunoassays for detection of staphylococcal enterotoxins A, B, C, E and F (toxic shock factor). In addition, with mitogenic assays using peripheral blood human lymphocytes as targets, we tested the activity of whole protein A as well as chromatographically separated fractions of several protein A preparations. In five protein A lots tested, we found significant quantities of all of the above 5 enterotoxins which represented up to 2% of the total protein. These preparations induced $C^{14}$ and tritiated thymidine incorporation in human peripheral blood lymphocytes. These activities were found to reside in HPLC fractions of whole protein A preparations ranging from 10,000 to 40,000 m.w. but not in the pure protein A peak. In four of the preparations, the predominant mitogenic activity appeared in the 20,000 to 30,000 m.w. range (the m.w. spectrum of enterotoxins).

Product 4: A tumor associated immune globulin preparation having tumoricidal activity and derived from the plasma of a tumor-bearing host which comprises predominantly IgG and IgM and which has titers of tumor associated antibodies at least twice that of serum from said host, increased Clq binding in fractions sedimenting beyond 7S on sucrose density gradient analysis, increase in void volume and decrease in included fraction proteins on Sephadex G-200, when compared to said serum. This is prepared from sera of tumor-bearing hosts by subjecting same to either a substantial increase or lowering of pH compared to normal plasma for an effective dissocating period.

Compared to untreated serum, tumor immune plasma has increased titers of tumor associated antibodies, increased Clq binding in heavy sedimenting fractions, and increased protein levels chromatographing C-200 in void volume with decreased levels in the included fractions.

Product 5: Zymosan activated plasma.

(a) Prepared by incubation of zymosan with normal or tumor-bearing serum, free of zymosan, which generates in vivo effects of peripheral vasodilatation and spasmogenic effects consistent with activity of complement by products.

Additional aspects and objects of the invention are methods for the generation and isolation of these novel products given above useful in the treatment of cancer. These include for Product 1 collection of an enriched immunoglobulin fraction (EIE) from forced flow electrophoresis of tumor bearing hosts which is then acidified or alkalinized, for Product 2 tumor immune gamma globulin preparation prepared by acidification of Cohn fractionated gamma globulin obtained from tumor bearing hosts, and for Product 3 protein A-IgG complex preparation prepared by incubating Protein A and IgG together, by precipitating them with polyethylene glycol or ammonium sulfate, or by polyethylene glycol precipitation of effluent from protein A collodion charcoal columns and other precipitation procedures known to those skilled in the art.

In addition to the foregoing aspects and objects, the inventions include specific combinations of steps which show tumor killing effects including the following:

Regimen 1: Administration of Product 1 with protein A followed by L-asparaginase and/or cytotoxic agents such as cyclophosphamide or adriamycin.

Regimen 2: Infusion of complement activated serum (Product 6) and acidified plasma (Product 4) on two successive days followed by L-asparaginase or cyclophosphamide on day 4.

Regimen 3: Infusion of Product 2 plus complement activated serum (Product 5) on two successive days followed by L-asparaginase and cyclophosphamide on day 4.

Regimen 4: Infusion of Products 3 and 5 on two successive days followed by cyclophosphamide and/or adriamycin on day 4.

Regimen 5: The use of L-asparaginase and cyclophosphamide on day 1 followed by infusion of Product 5 components and autologous acidified plasma (Product 4) on days 2 and 3.

Regimen 6: Infusion of protein A plus Product 5 and heterologous anti-tumor anti-serum.

Regimen 7: Infusion of Product 3 plus heterologous anti-tumor anti-serum.

Regimen 8: Protein A infused alone.

In addition, each of the Products 1, 2, 3, 4 and 5 and protein A, alone or combined, such as indicated above, are useful in treatment of hosts having cancer.

Other and further aspects, objects, features and advantages of the invention are given throughout the specification and the claims.

BRIEF DESCRIPTION OF THE DRAWINGS

FIG. 6A and 6B are a plasma fractionation method for preparation of anti-tumor IgG.

DESCRIPTION OF PREFERRED EMBODIMENTS

The present invention comprises novel products, their preparation and methods for the treatment of cancer, such as lymphomas and solid tumors, by which significant tumor reductions are obtained.

Preferred Embodiment: Product 1

Forced Flow Electrophoresis (FFE) And Enriched Immunoglobulin Effluent (EIE)

Figure 1:
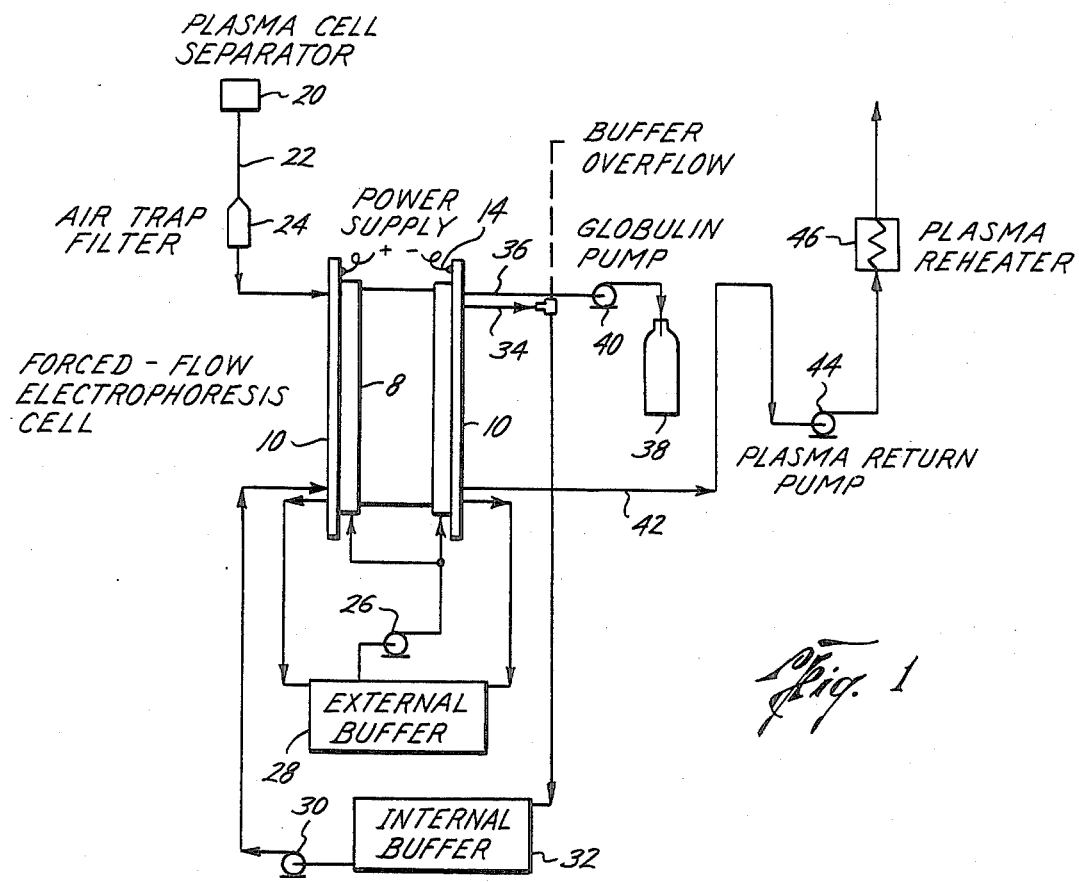
FIG. 1 is a flow diagram illustrating forced flow electrophoresis useful in preparing the enriched immunoglobulin effluent (EIE).
Figure 2:
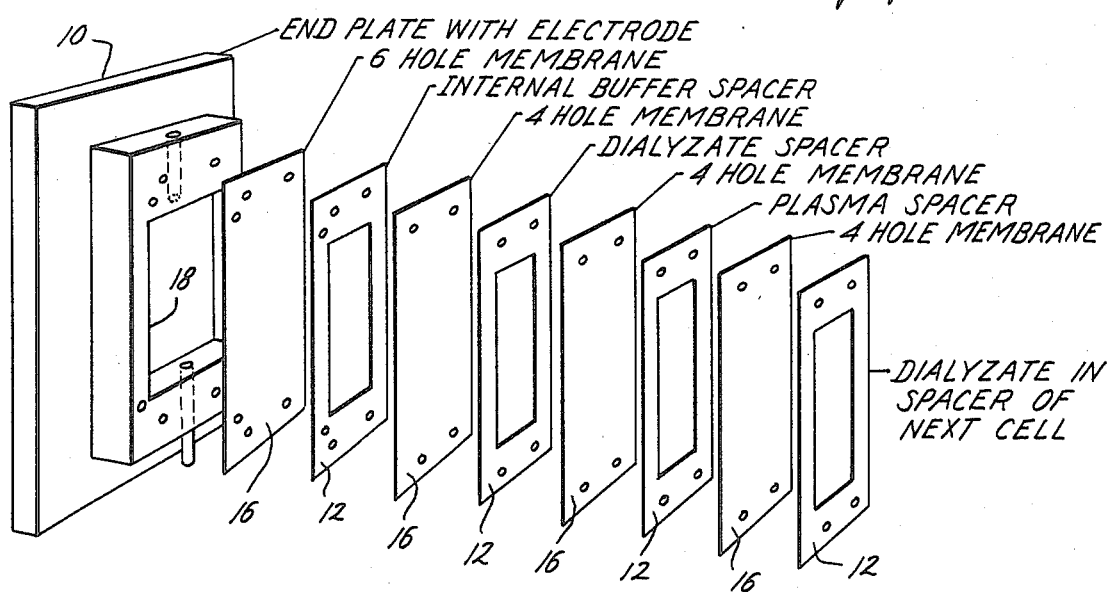
FIG. 2 is an expanded partial view of the forced flow electrophoresis cell.

Product 1 can be made by forced flow electrophoresis followed by acidification and alkalinization or other dissociative technique. Referring to FIG. 1, the forced flow electrophoresis cell pack 8 contains plastic end plates 10 which hold together a series of spacers 12 (FIG. 2) and has means for blood and buffer circulation as well as connectors 14 for direct current power supply (not shown). Parallel membranes 16 held in place by means of spacers 12 form a series of narrow channels across which the electric field is established. Four types of compartments can be recognized: The two recesses 18 in the endplates 10 house the platinum electrodes (not shown) and serve for external buffer circulation; an additional channel serves for the circulation of an internal buffer; an additional channel contains the flowing blood, plasma or sera and is separated from the globulin output by means of the membranes or filters 16. The membranes 16 employed are Visking regenerated cellulose membranes, analogous in properties to the Cuprophan membranes employed in artificial kidney work but mechanically more resistant. Millipore filters of 3.0 and 0.45 micron porosity were employed for the fractionation. Electrophoretically, all negatively charged blood components will be transported in any direction counter-current to that of liquid flow. It is the balance of these two vectors which determines the quality of fractionation. The purity of the fraction removed depends largely on the rate of filtration of globulin fraction and the voltage applied. Usually, the fastest possible removal of gamma globulin is desired and as a result contamination with other plasma proteins is obtained. If no voltage is applied no filtration of plasma proteins is achievable through the millipore filter. In all the experiments a cell assembly with four blood spacers was employed, the flow being in parallel. Each spacer has an effective area of 500 cm$^2$. The internal buffer spacers are injection-molded with protruding ribbed structures which compress the plasma input spacers to an average plasma film thickness of approximately 0.030 inches thereby limiting the total plasma volume of the apparatus to about 200-250 ml. The Vexar screening prevents the collapse of the membranes in the globulin output compartment. Pressure in the plasma components has to be higher than that of any of the other channels. A voltage gradient of 6-8 volts/cm results in current density of 0.02-0.4 amps/cm$^2$. Plasma flow is kept at 15-20 ml/spacer while internal blood flow is about 5X larger. The rate of gamma globulin withdrawal varies between 1.5 and 2.5 ml/spacer.

FIG. 1 is a flow diagram of a forced flow electrophoresis cell which illustrates operation of the device. A plasma separator 20 of any conventional or preferred type is connected by line 22 through an air trap filter 24 to the cell pack 8. External buffer is pumped by the pump 26 from the external buffer container 28 to the cell 8 and back again as shown by the arrows on the connecting lines. Internal buffer is pumped by the pump 30 from the internal buffer container 32 to the cell 8 and back as indicated by the arrows on the connecting lines. An external buffer overflow line 34 is provided to return overflow internal buffer to the internal buffer container 32.

An enriched EIE is collected from the cell 8 in line 36 and pumped into the container 38 by the pump 40. Plasma is returned from the cell 8 in line 42 and by pump 44 and preheated in the plasma preheater 46.

The use of this device in a dog with spontaneous cancer is as follows: An artery and vein are cannulated with catheters or needles and whole blood is pumped into the continuous flow plasma-cell-separator. Here whole blood is partitioned into formed elements and plasma by the plasma-cell separator 20. Plasma is then pumped into the FFE cell 8 at a rate of 5-15 ml/minute. In the FFE cell 8, plasma is subjected to electric current as described above and an EIE is collected in the container 38. Plasma emerging from the FFE cell 8 is then reunited with the formed elements (not shown) and is passaged back into the host. In a routine treatment approximately 1 calculated blood volume is passaged through this unit at a flow rate of 10-15 ml/min and an EIE of approximately 40 ml/lb of dog is collected.

The EIE collected from the FFE is then subjected to the following biochemical procedure: The pH of the EIE is titrated to 3.0 with 10N HCl, held for 5 minutes and then rapidly neutralized to 7.4 by drop-wise addition of 10N NaOH. Any precipitate which develops is rapidly removed by centrifugation at 1500× g for 30 minutes at 4° C. The EIE is then passaged through a 0.45 and a 5 micron pleated membrane filter and then returned intravenously to the host at a flow rate of 2 ml/minute.

After treatment with acid and neutralization, the EIE shows a marked increase in tumor associated antibodies measured by indirect immunofluorescence using the dog's own tumor as substrate. Results of this treatment are shown in Table IA. Biochemical characterization of the EIE after acidification shows a decrease in levels of IgG, IgM and immune complexes measured by laser nephelometry (93) compared to unacidified samples (Table IB). In addition, when untreated and acidified samples are subjected to sucrose density gradient fractionation and the various fractions analyzed for Clq binding, increased Clq binding levels in acidified samples compared to untreated EIE appear in fractions sedimenting beyond the 7S marker.

TABLE I-A

TUMOR ASSOCIATED ANTIBODIES IN EIE FROM FORCED FLOW ELECTROPHORESIS*

| | | Canine Lymphoma EIE | |
|---|---|---|---|
| Dog # | Disease | Untreated EIE | Acid Treated EIE |
| 1 | Lymphoma | 20,000 | 100,000 |
| 2 | Lymphoma | 10,000 | 130,000 |
| 3 | Lymphoma | 20,000 | 120,000 |

*Figures represent end point dilutions which gave positive fluorescence against the dog's own tumor substrate. Reactions in untreated and treated sera against canine hemangiosarcoma as substrate ranged from 1:10 to 1:50. Above reactions were reduced to 1:50 by prior incubation of unconjugated goat anti-canine IgG before addition of fluorescein labeled goat anti-canine IgG.

TABLE I-B

EFFECTS OF ACIDIFICATION OF EFFLUENT FROM FFE
Canine Immune Reactants

| EIE # | IgG (mg/dl) Pre | IgG (mg/dl) Post | IgM (mg/dl) Pre | IgM (mg/dl) Post | Immune Complexes (μg Eq/ml) Pre | Immune Complexes (μg Eq/ml) Post |
|---|---|---|---|---|---|---|
| 1 | 64.0 | 30.2 | 73.6 | 71.9 | 10.8 | 1.8 |

(Immune Reactants measured by laser nephelometry)

Use Of FFE And EIE (Acidified) In Treatment Of Spontaneous Canine Lymphoma (Regimen 1, Table XIII)

Gross Morphologic Changes And Toxicity After Treatments

In all dogs tested, within 4 hours after passage of a single plasma volume through the forced flow electrophoresis apparatus and collection of approximately 400 ml of effluent, tumor masses became warm and edematous. Twelve hours later, acidified EIE (10 ml/kg) plus protein A (8 μg/lb) was infused. Within 4 hours, lymph nodes became even more hyperthermic and edematous. Forty-eight hours later, the animals were given L-asparaginase and cyclophosphamide. Tumor regressions noted over the ensuing days reached levels of 66–95% below pre-perfusion levels and lasted from 15 days to 5 months with a mean of 45 days. Dogs treated with FFE and administration of acidified EIE plus protein A showed regressions of 20–35% which lasted for a mean of 6–8 days. Animals receiving L-asparaginase and cyclophosphamide alone showed regressions of 18–25% which lasted 8–10 days only. Dogs receiving protein A alone showed no significant regressions. Hence, the tumor killing response was substantially greater for those animals receiving the total regimen compared to the immunotherapeutic or chemotherapeutic programs alone. Results are shown in Table II.

of nuclei, granulation of cytoplasm and widening of intercellular spaces. Inflammatory cells were not prominent in these specimens at this time. Specimens obtained after administration of acidified EIE and protein A showed more pronounced changes in tumors exemplified by ballooning of cytoplasm, hyperlucency of cytoplasmic contents, clumping of chromatin and nucleoli with blurring of intercellular spaces, findings which denote sublethal and lethal changes in tumor cells. There was minimal associated inflammatory cell infiltration. In specimens obtained approximately 7 days after the outset of treatment, there was evidence of extensive necrosis in malignant lymph nodes with evidence of ghosts of tumor cells and focal infiltration by neutrophils.

Tumor Associated Antibodies, C'3 And Immunoglobulin Levels After Treatment

Before treatment, tumor associated antibodies were either undetectable or barely detectable in sera from hosts having cancer. Within 12 hours after treatment by forced flow electrophoresis, there was an increase in tumor associated antibodies measured by immunofluorescence. This was not evaluated further since animals were passively given EIE containing tumor associated antibodies. Serum C3 and IgG levels declined 12 hours after forced flow electrophoresis treatment in all dogs tested but rebounded above pre-treatment levels in the ensuing 48 hours. Immunoglobulin M levels did not change significantly.

Hematologic And Serologic Changes

Evaluation of leukocyte, platelet counts and hematocrits showed no significant changes in these parameters before and after completion of the 4-day regimen. In addition, there were no significant changes in serum sodium, potassium, chloride, calcium, phosphorous, SGPT, SGOT, BUN or creatinine after treatment.

TABLE II

RESPONSES TO IMMUNOCHEMOTHERAPY

| | | | Forced Flow Electrophoresis EIE (Acidified), Protein A Cyclophosphamide-L-Asparaginase | | | | Cyclophosphamide-L-Asparaginase | | | |
|---|---|---|---|---|---|---|---|---|---|---|
| Dog # | Tumor (Histology) | Breed | Bidimensional Product PreTX | Bidimensional Product PostTX | Tumor Reduction (%) | Remission Duration (Days) | Bidimensional Product PreTX | Bidimensional Product PostTX | Tumor Reduction (%) | Remission Duration (Days) |
| 1 | Histiocytic Lymphoma | Great Dane | 170.2 | 23.5 | 86.2 | 16 | 149.8 | 112.6 | 24.8 | 8 |
| 2 | Lymphocytic Lymphoma | German Shepherd | 86.2 | 19.8 | 77.0 | 41 | 150.2 | 83.1 | 44.7 | 17 |
| 3 | Histiocytic | Doberman | 165.7 | 53.8 | 67.5 | 21 | 94.1 | 72.6 | 22.8 | 9 |
| 4 | Histiocytic Lymphoma | German Shepherd | 52.0 | 4.3 | 91.7 | 121+ | | | | |
| 5 | Histiocytic Lymphoma | Afghan Hound | 110.8 | 9.7 | 91.2 | 30 | | | | |
| 6 | Hystiocytic Lymphoma | German Shepherd | 107.7 | 28.1 | 73.9 | 20 | | | | |

In all dogs, temperature elevations from 103°–107° C. were noted shortly after electrophoresis treatment which generally remitted within 6 hours after perfusion. Cultures of blood taken during febrile periods in 4 dogs revealed no bacterial growth.

Microscopic Changes at Various Intervals After FFE, EIE (Acidified) and Chemotherapy Tumor biopsies were obtained from all animals at various intervals after treatment. In biopsies taken from dogs after treatment by FFE at a time when the lymph nodes were edematous, there was evidence of pyknosis

Preferred Embodiment: Product 2

Tumor Immune Globulin Preparation

Figure 6A:
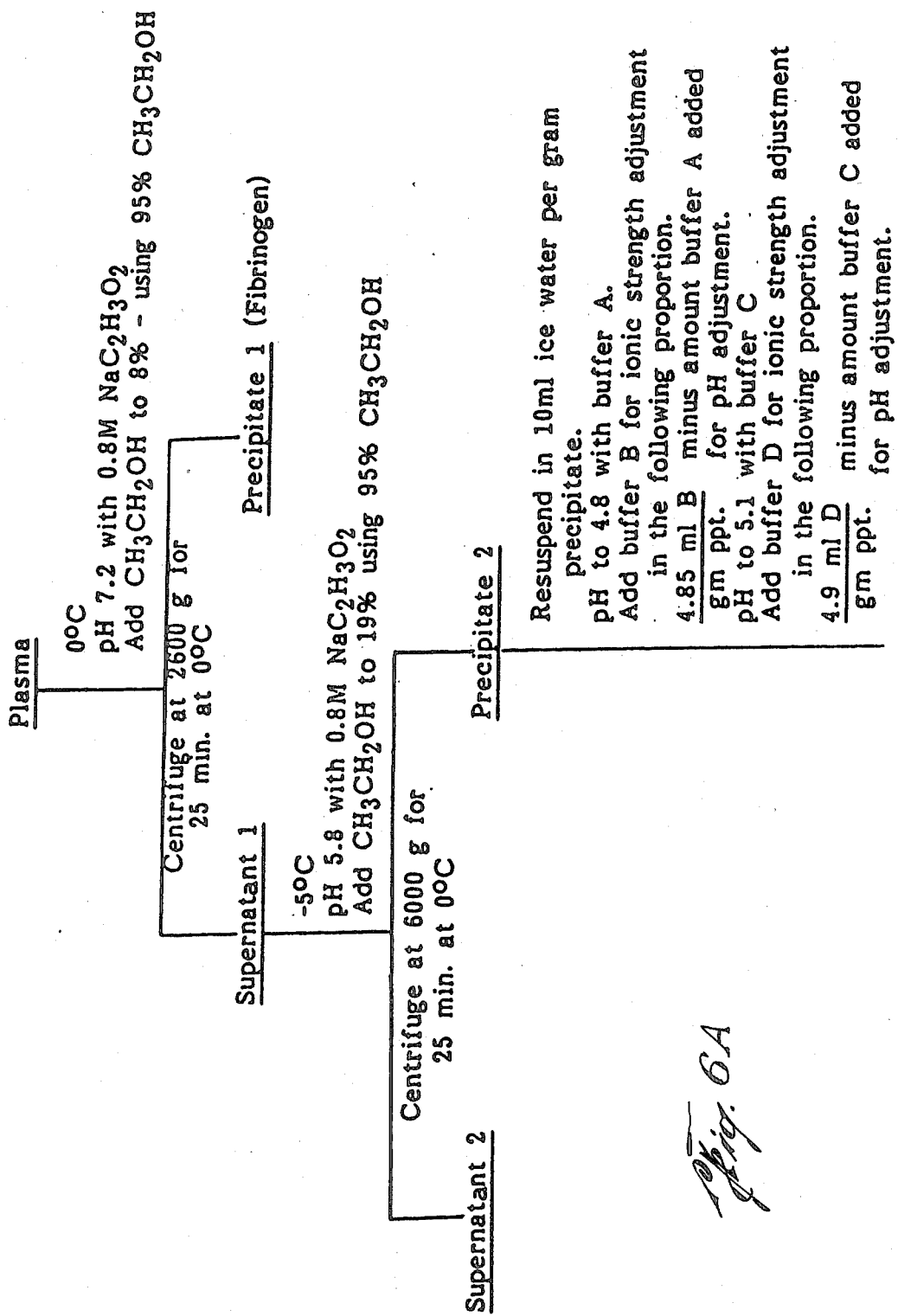

Product 2 (Tumor Immune Globulin Preparation) suitable for intravenous use can be prepared from the sera of tumor bearing hosts by modifications of methods previously described by Cohn, et al (94) and Kistler and Nitschmann (95). The method is outlined in schematic form in FIGS. 6A and 6B. The method of plasma fractionation is given as follows:

Plasma Source

Plasma was derived from peripheral whole blood of human patients. Approximately 500 milliliters of plasma collected in acid citrate dextrose were derived and clarified by centrifugation at the rate of 2600 g for 20 minutes at 0° C.

Preparation of Precipitate 1

The pH of the clarified plasma is determined and adjusted to 7.2 if necessary by the addition of 0.8M sodium acetate pH 4.0 buffer while maintaining the temperature at 0° C.

Forty-six milliliters of cold 95% ethanol is slowly added to the clarified plasma to achieve a final ethanol concentration of 8%. The suspension is cooled during the addition to achieve a temperature of 0° C. The visible precipitate comprised mostly of fibrinogen is removed by centrifugation of 2600 g for 20 minutes at 0°–4° C. The removed paste is called precipitate 1.

Preparation of Precipitate 2

A 2 ml aliquot of the precipitate 1 supernatant is titrated to pH 5.8 with 0.8M sodium acetate pH 4.0 to determine the quantity of sodium acetate buffer required to achieve a pH of 5.8 in the supernatant suspension. The total suspension is then adjusted to pH 5.8 with the same buffer.

Approximately 72 ml of cold 95% ethanol is added to pH 5.8 suspension to achieve a final ethanol concentration of 19%. The suspension is cooled during the addition to −5° C. The suspension is gently stirred for 30 minutes following the completion of the ethanol addition and the pH of the solution is maintained at 5.8. The suspension is then centrifuged at 6000×g for 25 minutes at 0° C.

The paste is harvested from the centrifuge bowls and weighed. This paste is labeled precipitate 2.

Preparation of Supernatant 3

Precipitate 2 paste is resuspended in 10 ml ice water per gram precipitate. About 25% of the water should be in the form of fine ice crystals. This suspension is allowed to become quite uniform. The pH of the suspension is adjusted to 4.8 by adding a pH 4.0 buffer composed of 1 volume of 0.05M $Na_2HPO_4$ and 6 volumes of 0.05M acetic acid (buffer A). The ionic strength is then increased by adding pH 4.8 buffer composed of one volume of 0.05M acetic acid (buffer B). The amount of this buffer needed is 4.85 ml per gram precipitate 2 minus the volume of pH 4.0 buffer A added previously for pH adjustment.

For the fractionation, the pH of the suspension is then raised to pH 5.1 by adding a pH 6.2 buffer made up of 1 volume of 0.05M $Na_2HPO_4$ and 0.833 volume of 0.05M acetic acid (buffer C). The ionic strength is then readjusted by the addition of a pH 5.1 buffer composed of 1 volume of 0.05M $Na_2HPO_4$ and 1.25 volumes of 0.05M acetic acid (buffer D). The amount of buffer D needed is 4.9 milliliters per gram precipitate 2 minus the volume of the buffer C used for pH adjustment. Finally, the suspension is diluted to a total volume of 19.5 milliliters per gram precipitate 2 with ice water. Cold 95% ethanol is then added to the suspension to achieve a total ethanol concentration of 12%. The suspension is maintained at 0° C. for 30 minutes followed by centrifugation at 14,000×g for 25 minutes at 0° C. The precipitate is discarded and the supernatant saved and labeled supernatant 3.

Preparation of Gamma-Globulin Precipitate

The ionic strength of supernatant 3 is then increased to 0.04 with concentrated NaCl using a relative salt conductivity meter.

A 2 ml aliquot of supernatant 3 is titrated to pH 7.2 with 1N NaOH in order to determine the quantity of 1N NaOH required to adjust the pH of the entire suspension. 1N NaOH is then added to the suspension in the appropriate amount to bring the pH to 7.2.

Ninety-five percent ethanol is then added to achieve a total ethanol concentration of 25%. The suspension is cooled to −7° C. during this addition. The suspension is allowed to stir gently for 30 minutes at −7° C. followed by centrifugation at 15,000×g for 30 minutes at −7° C. The precipitate here is the gamma globulin fraction desired.

Preparation of Tumor Immune Globulin

The paste containing gamma globulin is resuspended in phosphate buffered saline (PBS) and made 0.3M in glycine buffer. The pH is then lowered to 2.5 with 0.1N HCl. The suspension is then incubated for 5 minutes at 27° C. followed by neutralization to pH 7.3 with 0.1N NaOH. The preparation is then passed through a 2 micron filter and administered I.V. at 5 cc per minute.

Physico-Chemical Characteristics of Tumor Immune Globulin

Tumor immune globulin (acidified Cohn fraction) analyzed by laser nephelometry (93) is comprised of IgG with a small amount of IgA but no IgM or C3. Compared with unacidified Cohn fraction, there is less IgG and IgA (Table IV).

TABLE IV

| Serum Source | EFFECT OF ACIDIFICATION ON COMPOSITION OF COHN FRACTION* | | | | | | | |
|---|---|---|---|---|---|---|---|---|
| | IgG (mg/dl) | | IgA (mg/dl) | | IgM (mg/dl) | | C3 (mg/dl) | |
| | Before | After | Before | After | Before | After | Before | After |
| Breast Cancer | 1032 | 960 | 25.1 | 19 | 0 | 0 | 0 | 0 |
| Normal | 5904 | 3192 | 41.0 | 32.8 | 0 | 0 | 0 | 0 |

*Studies performed by laser nephelometry as previously described (96).

Tumor associated antibodies were analyzed in each of 2 batches of tumor immune globulin obtained from 2 humans with breast adenocarcinoma. Employing indirect immunofluorescence against a breast carcinoma substrate, titers of end point fluorescence exceeded 1:70,000 in both samples tested. Unacidified samples of the same batches showed end point titers of less than 1:50,000.

Figure 3:
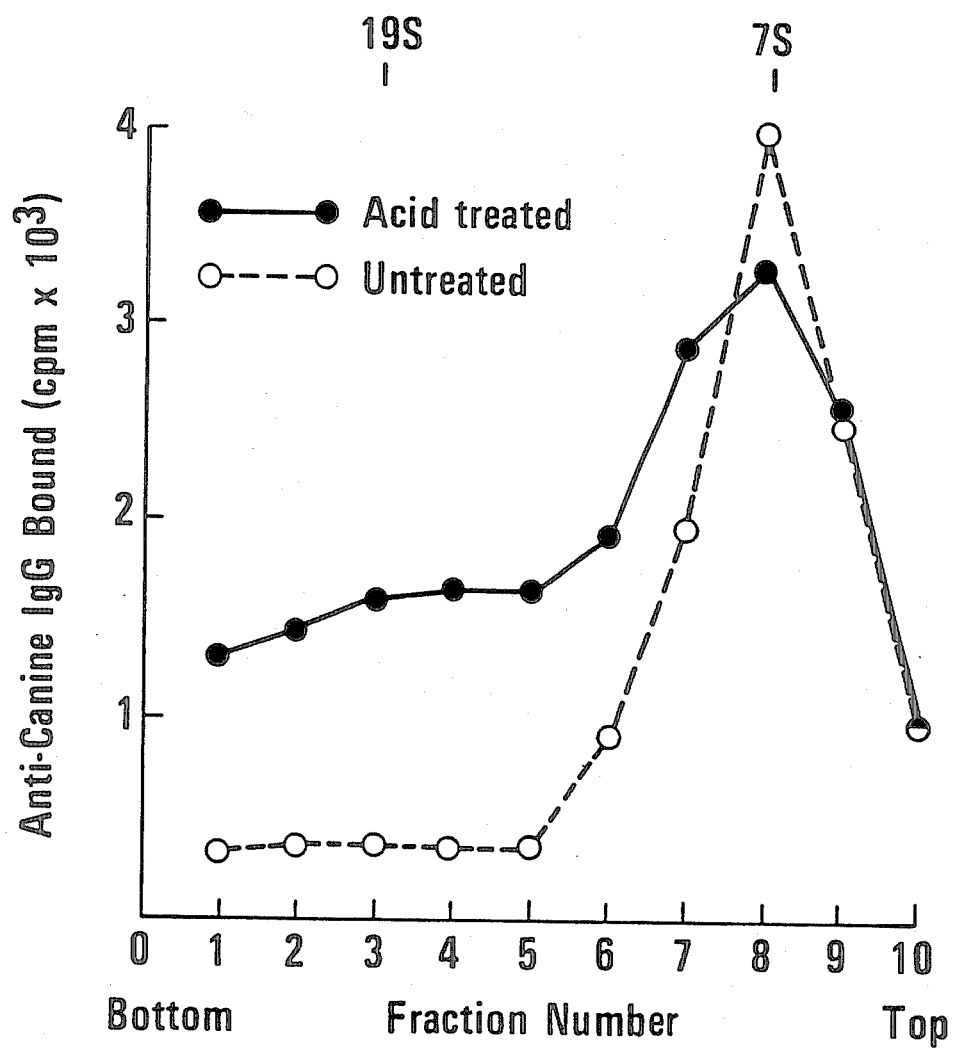
FIG. 3 is a graph illustrating Clq binding in sucrose density gradient fractions after acid treatment of tumor bearing sera.
Figure 4:
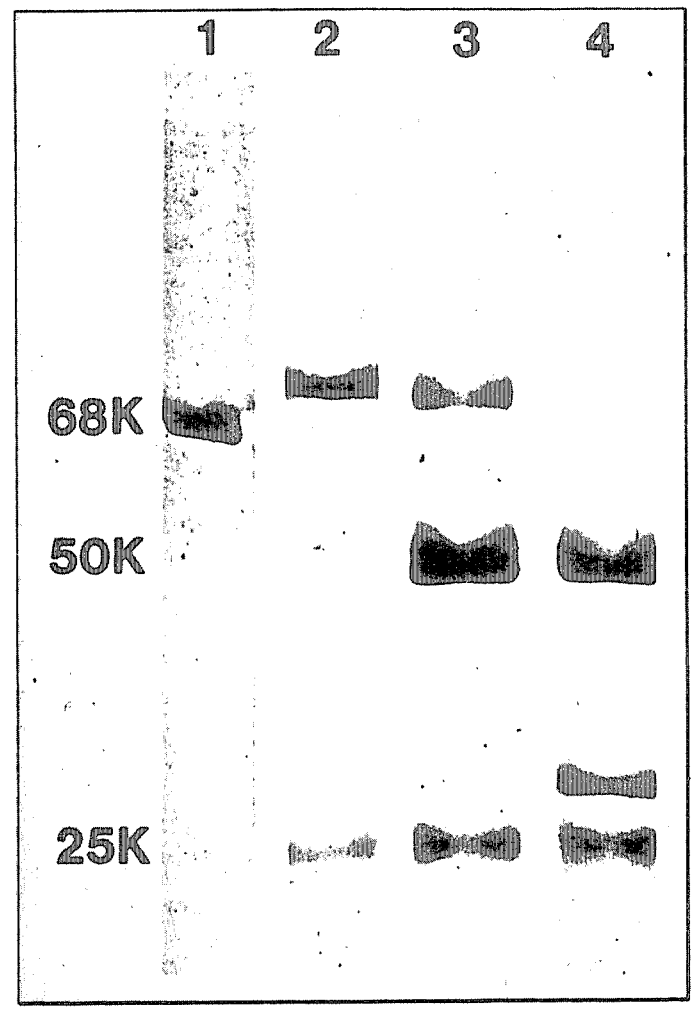
FIG. 4 is a photograph of a Coomassie Blue stained PAGE profile of isolated high molecular weight post-perfusion canine IgG.
Figure 5:
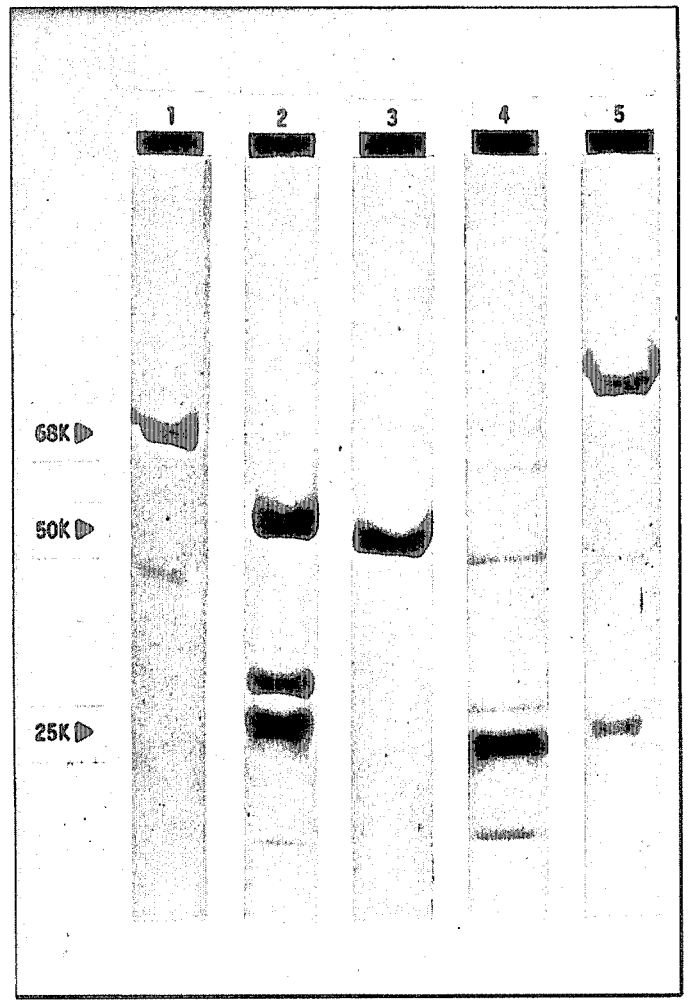
FIG. 5 is a photograph of a Coomassie Blue stained PAGE profile of protein A isolate from post-perfusion serum.

Tumor immune globulin was tested for tumor specific binding to MCF-7 breast adenocarcinoma cells by radioimmunoassay in fractions obtained from sucrose density gradient and compared with fractions from unacidified Cohn fraction. The tumor immune globulin showed an increase of tumor associated binding activity in fractions beyond the 7S marker. Similarly, Clq binding increased in fractions greater than 7S compared to unacidified fractions (FIG. 3). Hence, both tumor associated binding and Clq binding shifts to heavy (>7S) sedimenting fractions after acidification in the tumor immune globulin. Anti-complementary activity of tumor immune globulin tested by the method of Romer, et al (96) was less than for the unacidified fraction in a range comparable to that of other intravenous gamma globulin preparations (Table V).

TABLE V

ANTICOMPLEMENTARY ACTIVITY OF ACIDIFIED COHN FRACTION

| Protein Concentration (Mg) | Hemolysis (%) | | | |
|---|---|---|---|---|
| | Breast Cancer | | Normal | |
| | Before | After | Before | After |
| 1.0 | 3 | 75 | 2 | 10 |
| 0.5 | 10 | 85 | 4 | 35 |
| 0.25 | 12 | 88 | 14 | 53 |

Studies performed by method of Romer (96). Positive control with no sera induced 100% hemolysis. Aggregated IgG induced anti-complementary activity less than 1.

The functional capability of tumor immunoglobulin prepared from autologous tumor bearing sera was demonstrated upon infusion of 400-500 mg together with zymosan activated normal canine serum (Regimen 3, Table XIV) into tumor bearing hosts. Shortly after infusion into 2 dogs, one with spontaneous mammary adenocarcinoma and one with melanoma, acute necrosis of tumor sites was noted characterized by hyperemia and gross necrosis of ulcerated areas of tumor. Microscopically, tumorous sites showed diffuse necrosis of tumor cells with focal areas of neutrophil infiltration.

Preferred Embodiment: Product 3

Protein A-IgG Preparation

Protein A-IgG complexes (Product 3) may be prepared by perfusing 5-50 ml of plasma from hosts having cancer or normal plasma over protein A from *staphylococcus aureus* Cowans I (containing 1.0 mg of immobilized protein A) immobilized in collodion charcoal or it may be isolated from the effluent sera by addition of 5% polyethylene glycol or other procedures for precipitating high molecular weight protein known to those skilled in the art. The resultant precipitate is resuspended in normal saline and dialyzed against phosphate buffered saline after which it is administered I.V. to tumor bearing hosts. The method is shown in Table VI.

TABLE VI

POLYETHYLENE GLYCOL PRECIPITATION METHOD FOR ISOLATION OF PROTEIN A-IgG COMPLEXES

1. Three ml of serum or plasma emerging from protein A collodion charcoal columns is mixed with 1 ml of 20% PEG (PEG 6000, Fisher Scientific Co., Fairlawn, NJ) and incubated at 25° C. for 1 hour.
2. PEG precipitate is obtained by centrifugation at 3,000×g, at 4° C. washed twice in 5% PEG, dissolved in PBS, and dialyzed extensively against PBS at 4° C.

Protein A-IgG complexes may be prepared without use of the protein A collodion charcoal columns by incubating protein A (10-1000 µg) with normal serum or plasma (1-3 ml) or IgG (1-10 mg) for 30 minutes at 27° C. adding an additional volume (5-10 ml) of normal saline and then infusing this mixture I.V. into tumor bearing hosts. The following Table VII illustrates a further method of preparing protein A-IgG complexes.

TABLE VII

PREPARATION OF PROTEIN A-IgG COMPLEXES

1. Protein A (10-1000 µg) is incubated with 1-10 mg of IgG in PBS for 30 minutes.
2. PEG at 27° C. is added to a final concentration of 5% and the mixture is centrifuged at 5000×g for 30 minutes at 4° C.
3. The precipitate is resuspended at 20 ml of saline and dialyzed against PBS for 2 hours to remove PEG.
4. The solution is brought to a final volumne of 5-10 ml and injected intravenously.

Physico-Chemical Characteristics Of Protein A-IgG Complexes Emerging From Protein A Collodion-Charcoal (PACC) Columns or Immobilized *Staphylococcus Aureus* Cowans 1 (SpA) Columns (SAC)

Sera from dogs with spontaneous mammary carcinoma were perfused over SpA immobilized in a microporous membrane filter (0.2 micron) or protein A collodion charcoal. The following was noted.

RESULTS

Changes in Clq Binding in Sera After Perfusion Over SAC or PACC

Sera from 5 normal dogs and 6 dogs with mammary adenocarcinoma were perfused over SAC and pre and post-perfusion samples were assayed for levels of Clq binding activity by radioimmunoassay as described. There was a consistent increase in Clq binding above pretreatment values (Table VIII). The initial decrease in Clq binding may represent a dilutional effect and/or removal of Clq binding immune complexes and IgG by Protein A Collodion Charcoal (PACC). In general, the levels of Clq binding in pre-perfusion tumor bearing serum were higher than in pre-perfusion normal serum and the net increases in the tumor bearing sera were greater (mean increase: 382±378 S.D. µg ACG equivalents/ml) than for normal serum (means increase: 114±186 S.D. µg ACG equivalents). In contrast to the observed increases in Clq binding activity, in serum perfused over SAC, canine IgG concentrations were uniformly reduced below pre-perfusion levels as were post perfusion levels of IgM (Table VIII).

TABLE VIII

Changes in Clq Binding After Serum Perfusion Over Immobilized SpA

| Sample # | Pre | Post | |
|---|---|---|---|
| | | # Fractions Tested | Net Increase* (µg ACG equivalents) |
| Normal Canina Sera | | | |
| 1 | 40 | 8 | 480 |
| 2 | 16 | 4 | 22 |
| 3 | 16 | 4 | 62 |
| 4 | 19 | 4 | −5 |
| 5 | 14 | 4 | 6 |
| | | | Mean 114 ± 186 |
| Tumor Sera | | | |
| 1 | 60 | 8 | 831 |
| 2 | 87 | 6 | 978 |
| 3 | 37 | 8 | 4 |
| 4 | 41 | 4 | 132 |
| 5 | 48 | 4 | 103 |

TABLE VIII-continued

Changes in␣C1q Binding After Serum Perfusion
Over Immobilized SpA

| Sample # | Pre | Post # Fractions Tested | Post Net Increase* (μg ACG equivalents) |
|---|---|---|---|
| 6 | 70 | 4 | 243 |
| | | | Mean 382 ± 378 |

*Preperfusion values were multiplied by the number of fractions collected in the effluent and subtracted from the cumulative ACG equivalents in these fractions. 100 ml of normal or tumor-bearing sera were perfused over SAC and 1 ml fractions collected and tested for C1q binding activity.

To determine if protein A on the SAC might be important in the generation of increased C1q binding, sera from normal dogs and dogs with mammary adenocarcinoma were perfused over SAC or protein A deficient *Staphylococcus Aureus* Strain Wood 46 (SAW) as described in Methods and effluent samples tested for C1q binding. Samples emerging from the SAC columns showed an increase above pre-perfusion C1q binding levels whereas effluent samples from the SAW columns showed minimal changes from pretreatment levels. As with the above studies, the initial decline in C1q binding partially reflected dilutional effects and immune complex removal by the SAC or SAW.

Sera from normal dogs and dogs with mammary adenocarcinoma over PACC as described in Methods. In 7 of 7 tumor bearing sera and 5 of 7 normal sera there was an increase in C1q binding in effluent sera (Table IX). In contrast to perfusion over SAC, there were no significant changes in IgG, IgM, IgA levels in sera perfused over PACC (Table IX).

TABLE IX

SOLID PHASE C1q BINDING* BEFORE AND AFTER PERFUSION OF SERA OVER PACC

| NO. | NORMAL SERA | NO. | TUMOR BEARING SERA |
|---|---|---|---|
| 1 | pre 50.9 (50–51.8) | 1 | pre 60.5 (57.2–62.8) |
| | post 65.3 (62.6–68.8) | | post 73.0 (66.9–81.1) |
| 2 | pre 43.6 (35.4–47.4) | 2 | pre 49.7 (45.1–52.2) |
| | post 63.2 (59.0–67.4) | | post 69.6 (58.4–80.0) |
| 3 | pre 58.9 (57.3–60.6) | 3 | pre 50.0 (49.5–51.0) |
| | post 63.3 (60.0–66.7) | | post 57.0 (54.8–59.2) |
| 4 | pre 50.2 (43.6–53.0) | 4 | pre 42.2 (36.8–46.5) |
| | post 52.1 (47.9–55.2) | 4 | post 56.7 (53.9–59.5) |
| 5 | pre 41.7 (39.7–43.7) | 5 | pre 28.6 (26.8–30.5) |
| | post 55.8 (55.0–56.7) | | post 34.8 (32.6–37.1) |
| 6 | pre 26.9 (25.4–28.5) | 6 | pre 32 (32.0–32.1) |
| | post 33.8 (33.7–33.9) | | post 36.8 (34.5–39.1) |
| 7 | pre 29.6 (27.9–31.3) | 7 | pre 31.4 (31.1–31.8) |
| | post 30.8 (30.1–30.6) | | post 53.9 (52.7–55.1) |

*Ten ml of normal or tumor bearing sera were passaged over PACC and pre and post-treatment sera were analyzed for solid phase C1q binding. C1q binding is expressed as nanograms of anti-canine IgG bound. Figures represent the average volume from duplicate or triplicate samples. Parenthesized figures indicate range of values from duplicate or triplicate samples.

Partial Characterization of Complexes Generated in Sera After Perfusion Over PACC Since protein A has been shown to bind canine IgM and IgA, we tested for these components as well as IgG and C3 in the complexes in post perfusion sera. For this purpose pre and post perfusion sera were incubated with C1q coated tubes in order to bind the complexes. As a control, sera which has perfused over canine albumin rather than protein A immobilized in collodion charcoal was similarly incubated with C1q coated tubes. The tubes were washed and excess $125_I$ F(ab')$_2$ fragments specific for canine IgG, IgM, IgA or C3 were added and bound radioactivity measured. Post perfusion binding levels of anti-IgG and anti-IgM increased approximately 20% above pre-perfusion values but there were no significant changes in anti-IgA or anti-C3 binding. Results were similar for tumor bearing and normal sera and similar increases in anti-IgG binding activity were detected in post perfusion sera from an additional tumor bearing and normal dog. In contrast, IgG binding activity was reduced by 15% in serum perfused over canine albumin while binding of other components was essentially unchanged.

Normal or tumor bearing human sera was similarly passaged over PACC, incubated in C1q coated tubes and tested for binding of $125_I$ F(ab')$_2$ fragments specific for human IgG, IgM, IgA and C3. Results demonstrate increases in anti-IgG, IgM and C3 but not IgA binding.

To investigate the sedimentation characteristics of the C1q binding IgG generated in sera after perfusion over PACC, pre and post perfusion effluent samples from normal or tumor bearing sera were ultracentrifuged in sucrose density gradients and fractions assayed for C1q binding IgG. Both sera showed increased levels of C1q binding IgG in fractions greater than 7S compared to corresponding fractions from pre-perfusion sera. Similar increases in C1q binding in these gradient fractions were noted when F(ab')$_2$ fragments specific for gamma chains of canine IgG were used to detect bound IgG.

The high molecular weight IgG complexes in post perfusion canine sera were then isolated by fractionation on G-200 column chromatography and passage of the void volume peak fractions over an immunoadsorbent containing gamma chain specific rabbit anti-canine IgG. The retained protein was eluted, neutralized, concentrated and reduced before analysis by PAGE. PAGE profiles stained with Coomassie Blue revealed distinct 50,000 and 25,000 molecular weight polypeptides co-migrating with gamma and light chains of canine IgG. A lightly stained 75,000 molecular weight polypeptide co-migrating with the mu immunoglobulin chain of canine IgM was also observed and probably represents canine IgM present in the complex isolate. Ten μg of the isolated high molecular weight IgG complexes examined in double diffusion studies showed a single precipitin band with goat anti-whole canine serum which formed a line of identity with gamma chain specific rabbit anti-canine IgG. These studies indicated that a high molecular weight species containing canine IgG and IgM was formed during perfusion of sera over PACC.

Release of Protein A from PACC by Serum and Serum Components

Although high molecular weight C1q binding IgG was formed during perfusion of serum over PACC, PAGE analysis of eluates failed to reveal a band that could be unequivocally characterized as protein A since authentic protein A migrates to a position nearly coincident with canine gamma chains. Therefore, release of protein A into serum during perfusion was studied using trace labeled $125_I$ protein A in the PACC as a marker. The results show that $125_I$ protein A was released from PACC by perfusion of sera as well as solutions of albumin or IgG from 3 different species. In addition, the elution was not specific for protein A since the same solutions also released $125_I$ canine albumin that had been immobilized in collodion charcoal in a fashion similar to protein A. Based upon the amount of radioactivity released from the PACC it was estimated that 0.0025–0.005 mg (0.25–0.5%) of protein A was desorbed from 1 mg of immobilized protein A after perfusion of 10 ml of serum.

Protein A was further identified in serum perfused over PACC as follows: Post-perfusion PEG precipitates of sera perfused over PACC or SAC were fractionated on G-100 at pH 3.0. The included fractions (100,000 M.W.) were neutralized, concentrated and analyzed by PAGE. Coomassie Blue stained PAGE profiles of these samples revealed 2–4 distinct polypeptide bands one of which co-migrated with purified protein A.

In further studies, canine serum containing canine IgG was perfused over PACC containing $^{125}I$ labeled protein A as a marker. The post-perfusion serum was treated with 5% PEG to precipitate any $^{125}I$ protein A-IgG complexes and then analyzed by PAGE. A radioactive peak corresponding to the protein A marker was observed. Some lower molecular weight radioactive protein A species were also noted which might represent $^{125}I$ protein A fragments.

In additional studies, normal canine sera perfused over PACC were treated with 5% PEG to precipitate protein A-IgG complexes. The solubilized precipitate was fractionated on Sephadex G-100 under dissociating condition and the included fraction precipitated with $(NH_4)_2SO_4$. The redissolved precipitate was passed over Sepharose 4B to which human IgG was coupled. The bound material was eluted and concentrated. The presence of protein A in the eluate was suggested by double diffusion studies which showed a precipitin band with normal human serum but not normal chicken serum which does not bind to protein A.

Identification of Protein A in High Molecular Weight Complexes

To identify protein A in the high molecular weight sucrose density fractions of post perfusion effluent sera, the following study was performed. Normal canine sera was passaged over PACC and post perfusion sera containing eluted $^{125}I$ protein A was fractionated on sucrose density gradient. $^{125}I$ protein A was found in a broad range of fractions from 7S to 19S compared to free $^{125}I$ protein A which showed a peak below the 7S marker. This suggests that protein A is eluted from PACC in a high molecular weight form distinct from free protein A.

Post perfusion sera containing $^{125}I$ protein A was ultracentrifugated as described and its sedimentation characteristics compared with that of purified free protein A. Radiolabelled protein A in the post-perfusion samples was distributed in high molecular weight fractions of the gradient compared to free protein A. Parallel sucrose density gradient fractions of post-perfusion sera showed increased Clq binding IgG compared to pretreatment sera. This suggested that protein A which eluted from PACC into post perfusion sera was in complexes with immunoglobulins and may have contributed to the increased Clq binding observed in post perfusion sucrose density gradient fractions.

To determine if $^{131}I$ protein A eluted from PACC after serum perfusion could bind to Clq coated tubes, the following experiment was carried out: Ten ml of normal or tumor bearing sera were passaged over PACC containing $^{131}I$ protein A. The effluent samples containing eluted $^{131}I$ protein A were concentrated to a 10 ml volume and then 0.5 ml incubated with Clq coated tubes. Free $^{131}I$ protein A was employed as a control. Results demonstrate approximately 7 fold increase in binding of $^{131}I$ in PACC effluent compared to binding of free $^{131}I$ protein A. Hence, some of the protein A eluted from PACC after serum perfusion had acquired Clq binding properties suggesting that it was released in a form bound to immunoglobulins.

In additional experiments, normal or tumor bearing canine and human sera were perfused over PACC. Pretreatment and effluent samples (0.5) were incubated with Clq coated tubes. The tubes were washed and affinity purified $^{125}I$ chicken antiprotein A was added as described. Results showed significantly increased binding of anti-protein A in (a) 2 of 3 and 3 of 5 normal canine and human postreatment samples respectively, (b) 4 of 4 and 4 of 6 tumor bearing canine and human post perfusion samples respectively.

In further studies, 50 ml of normal canine sera were perfused through columns containing $^{125}I$ protein A or $^{125}I$ canine albumin together with unlabeled protein A immobilized in collodion charcoal. The effluent fractions containing the peak radioactivity were pooled. To 10 ml aliquots of these peaks, an equal volume of 50% $(NH_4)_2SO_4$, 5% PEG or 10% trichloroacetic acid was added. Results demonstrated that 70–80% of the $^{125}I$ protein A was precipitable with $NH_4SO_4$ and PEG compared to only 5–10% of free protein A. In contrast, less than 10% of released albumin was $(NH_4)_2SO_4$ or PEG precipitable. These findings suggest that protein A but not albumin emerges in post perfusion effluent complexed with immunoglobulins.

Molecular Formula of Clq Binding Complexes Containing IgG and Protein A

To determine if canine IgG from canine serum were bound together in Clq binding complexes present in post perfusion serum the following experiment was carried out: Ten ml of normal canine serum containing $^{131}I$ canine IgG was perfused over PACC containing $^{125}I$ protein A. The effluent was concentrated and then incubated with Clq coated tubes. Based on the specific activities of the labelled protein A and IgG, we calculated that the empirical formula of Clq binding complexes was close to $IgG_2PA$. The approximate molecular weight of these complexes was determined to be 680,000 by chromatography over Sepharose 6B. Based on these values and the empirical formula, the molecular formula corresponds to $[(IgG)_2 PA]_2$.

In the case of human serum, in addition to the high molecular weight peak corresponding to the complexes found in canine serum, a second peak appeared close to the molecular weight of IgG. This peak as well as the high molecular weight fraction showed Clq binding activity above control levels. Because of the difficulty of determining the molecular weight of complexes in this range with this method, a molecular formula for these small complexes cannot be assigned.

Preparation Of Protein A-IgG Conjugates In Vitro

Protein A-IgG conjugates were prepared at various molar ratios of protein A to IgG and were analyzed by nephelometry after incubation at 27° C. for 60 minutes. Maximum light scattering was observed at protein A-IgG molar ratios of 1 to 2. Lower values were present at molar ratios of 1 to 10 and greater. Complement fixing properties of protein A-IgG complexes prepared at varying molar ratios were studied in an anti-complementary assay (96). Maximum anti-complementary activity was noted at molar ratios of protein A to IgG from 1:100 to 1:1000. Protein A-IgG complexes prepared at various molar ratios were tested for capacity to induce acid protease, myeloperoxidase and beta glucuronidase release from canine neutrophils (98). The optimal protein A-IgG ratio for release of these enzymes was 1:100 with decreasing levels of cathepsin generation at ratios of 1:10 or less.

Specific Antibodies In PEG Precipitable IgG Generated During PACC Perfusion

Canine anti-serum specific for human erythrocytes and a canine anti-serum specific for MCF-7 human breast adenocarcinoma cells were prepared. Each of these sera and normal canine serum was treated with 5% PEG to remove immunoglobulin aggregates and endogenous immune complexes and then perfused over PACC. Post perfusion serum was treated with 5% PEG and the precipitated protein assayed for antibody activity against MCF-7 cells, murine fibrosarcoma cells (L-cells) and canine mammary adenocarcinoma cells. Tables X and XI show that after PACC perfusion, specific antibodies were recoverable in the PEG precipitable fraction of immune sera which exceeded levels in the PEG precipitable post perfusion fraction of normal serum.

TABLE X

SPECIFICITY AND ANTIBODY ACTIVITY OF CANINE ANTI-MCF-7 SERUM AFTER PERFUSION OVER PACC

| Sample | Ng Bound to MCF-7 | Ng Bound To Murine L Cells | Ng Bound to Canine Adeno-carcinoma |
|---|---|---|---|
| PBS* | 3.58 ± 0.350 | 2.51 ± 0.206 | 1.92 ± 0.133 |
| Normal Dog Serum | 20.58 ± 3.363 | 23.66 ± 2.754 | 9.40 ± 0.217 |
| Canine Anti-MCF-7 | 36.86 ± 0.066** | 27.15 ± 0.713 | 9.54 ± 1.157 |

*Phosphate Buffered Saline
**Significantly higher (P > 0.05) than normal dog serum.

TABLE XI

SPECIFICITY AND ANTIBODY ACTIVITY OF CANINE ANTI-RBC SERUM

| Sample | Ng Bound to Human RBC | Ng Bound To Murine L Cells | Ng Bound to Canine Adeno-carcinoma |
|---|---|---|---|
| PBS | 0.84 ± 0.037 | 0.063 ± 0.066 | 1.05 ± 0.181 |
| Normal Dog Serum | 7.31 ± 0.159 | 19.64 ± 2.108 | 7.80 ± 0.526 |
| Canine Anti-Human RBC Serum | 108.34 ± 0.188* | 18.06 ± 1.947 | 6.70 ± 0.058 |

*Significantly higher (P > 0.05) than normal dog serum.

To investigate the sedimentation characteristics of the antibody containing aggregates, post perfusion serum was subjected to sucrose density gradient ultracentrifugation and assayed for antibody activity by radioimmunoassay. Post perfusion anti-sera showed specific binding in fractions from 7S to 19S which exceeded binding of normal serum in these fractions.

Post perfusion canine anti-serum specific for human erythrocytes was precipitated with 5% PEG and tested for specific agglutination of human erythrocytes and compared with PEG precipitates from post perfusion normal canine serum. Table XII shows that canine anti-human erythrocyte sera caused significant agglutination reactions in contrast to agglutination with similar quantities of precipitates from normal canine serum.

TABLE XII

AGGLUTINATION REACTIONS OF POST PERFUSION PEG PRECIPITATES

| | Agglutination Score* Protein Quantity (μg) | | | |
|---|---|---|---|---|
| Sample | 50 | 25 | 10 | 5 |
| Normal PEG ppt. | 0 | 0 | 0 | 0 |
| Immune PEG ppt. | ++++ | ++++ | + | 0 |

*Agglutination reactions graded as 0 to ++++

Antibody Dependent Cellular Cytotoxicity (ADCC) Of Post Perfusion PEG Precipitates Post perfusion PEG precipitates from canine anti-human RBC and normal canine serum were used to coat human erythrocyte targets and assayed for ADCC using canine erythrocytes as effector cells. PEG precipitates from immune serum showed more than 300% greater cytotoxicity than normal serum at effector: target ratio of 1:1.

Role Of Complement In The Generation Of C1q Binding IgG During Perfusion Over PACC To determine if canine complement was essential for generation of the C1q binding IgG during serum perfusion over immobilized protein A, normal dog serum, heated or unheated at 56° for 60 minutes, was treated with 5% PEG to remove immunoglobulin aggregates then perfused over PACC. Heated and unheated sera showed comparable increases in C1q binding in post-perfusion effluent sera. Moreover, when normal or congenitally C3 deficient canine sera were similarly treated with 5% PEG and then perfused over PACC, similar quantities of C1q binding were generated. Hence, C1q binding IgG oligomers were generated in sera after perfusion over PACC by complement independent mechanisms.

Biologic Activities Of The High Molecular Weight PEG Precipitable IgG Generated During PACC Perfusion Normal and tumor bearing sera were treated with 5% PEG to remove immunoglobulin aggregates and endogenous immune complexes and then perfused over PACC. Post-perfusion effluent sample was then treated a second time with 5% PEG to precipitate the generated high molecular weight IgG. This was then assessed for various functional biologic activities.

To determine if the generated IgG oligomers containing protein A-IgG conjugates and post-perfusion sera could inhibit Fc dependent lymphocyte rosette formation, the PEG precipitated IgG oligomers in post-perfusion sera were incubated with canine lymphocytes which were then assayed for their capacity to form rosettes with sensitized human erythrocytes (99). PEG precipitable IgG oligomers in post-perfusion sera from normal or tumor bearing dogs showed comparable inhibition of rosette formation ranging from 28-31% compared to 47% inhibition by aggregated canine IgG.

To determine if the IgG oligomers containing protein A-IgG conjugates and post-perfusion serum could activate and consume complement, the PEG precipitated IgG oligomers in post-perfusion sera were incubated with a guinea pig complement source and then assayed for capacity to mediate lysis in a complement dependent hemolytic assay (96). The PEG precipitable IgG oligomers in post-perfusion serum from normal and tumor bearing dogs were comparable in their ability to activate and consume complement.

To determine if the IgG oligomers containing protein A-IgG conjugates from post-perfusion sera could stimulate superoxide anion release by human polymorphonuclear cells (PMN), the post-perfusion sera were incubated with PMN and medias assayed for superoxide generation by chemiluminescense (100, 101). PEG precipitable IgG oligomers in post-perfusion sera from normal and tumor bearing dogs were comparable in their ability to stimulate superoxide anion generation by canine PMNs.

The cytotoxic function of the PEG precipitates from post-perfusion sera was evaluated. PEG precipitable oligomers containing protein A-IgG conjugates from both tumor bearing and normal sera induced cytotoxicity which was nonspecific since a similar degree of lysis was observed when target cells such as mammary adenocarcinoma, murine L cell and human erythrocytes were employed. However, the cytotoxicity appeared to be complement dependent since C3 deficient sera generated significantly less cytotoxicity than did corresponding normal sera when tested against mammary carcinoma cells, murine L-cells, and human erythrocytes.

Biologic Activities of Synthetic Protein A-IgG Complexes

A. Chemiluminescense

Studies of chemiluminescense using synthetic protein A-IgG complexes have progressed. Synthetic complexes were initially prepared by adding protein A to serum or to pure canine or human IgG induced chemiluminescent activity. These complexes showed similar activity whether prepared in serum or by addition of protein A to pure human IgG. The supernatants from insoluble complexes prepared either from serum or IgG were essentially inactive. Controls including pure protein A, IgG and serum alone were inactive in chemiluminescense. Addition of a fresh complement source to complexes made either from serum or fresh IgG did not appear to significantly enhance chemiluminescense activity. In contrast, the complexes made from serum in the presence of EDTA were not as active in aggregometry as complexes made from serum in the absence of EDTA. Supernatants from complexes made either from serum or IgG were inactive. An unfractionated mixture of supernatant plus complexes or a mixture reconstituted from isolated precipitates and supernatants were more active than the precipitates alone. This indicates the presence of factors in the supernatant which are not active themselves but which are able to enhance the activity of the insoluble complexes.

(B) Aggregometry

Synthetic complexes have shown the following: incubation of the protein A-IgG complexes prepared either with IgG or serum with or without EDTA results in significant aggregation of granulocytes. However, the complexes made in the absence of EDTA are much more potent than those made in the presence of EDTA. The supernatants from these complexes are inactive but added back to the precipitates appeared to result in significant augumentation of activity equivalent to that of the unfractionated mixture. This finding suggests that the supernatant potentiates the activity of the insoluble complexes. In this regard, high levels of C3a and C5a have been detected by radioimmunoassay in the supernatants from the complexes. An important point in differentiating the activities is as follows: soluble complexes made by adding relatively high amounts of protein A into serum produces complexes that are not active in aggregometry but have levels of C3a and C5a comparable to supernatants from the insoluble precipitates.

(C) Complement Studies

Synthetic complexes containing protein A-IgG made either from serum or pure IgG activate whole complement activity either in dog or in human serum. Complement depletion amounts to 40 to 70% in dog. Insoluble complexes prepared either from human or dog serum or from C3 deficient dog serum, or human or dog IgG depletes >90% of whole complement activity as shown in Table XVII. Either insoluble or soluble complexes made from high levels of protein A added to serum generate up to 20-30 µg of C3a ml of serum. This approximates a 40% conversion of total C3 in serum to C3a. The same supernatants contain up to 800 ng of C5a/ml of serum. Complexes that have been washed and added to fresh serum continue to generate C3a and C5a activity. Once these complexes were prepared they appear to be able not only to generate C3a initially from serum in which they were prepared, but, upon entry into fresh serum, they are capable of generating additional C3a and C5a as well as shown in Table XVIII. For example, precipitates either from serum or pure IgG added to fresh serum generate up to 2500 ng of C5a/ml. In experimental studies, C5a is known to induce hypotension, vasodilatation and enhanced capillary permeability. Similar responses were documented in vivo under actue clinical conditions after perfusion treatments. Preliminary studies, showed elevated levels of C5a in serum samples of our patients obtained at a time after perfusion when pressures were declining. In an additional study in which no change in C5a levels were noted, there were no significant change in cardiovascular parameters. These findings suggested that anaphylatoxins generated from the PA-IgG conjugates might account in part for the observed cardiovascular effects.

In Vivo Effects Of Protein A-IgG Conjugates

Three dogs with spontaneous tumors were given protein A-IgG complexes (Regimen 9, Table XVIII) prepared by incubating 1 mg protein A with 3 ml of autologous serum for 30 minutes at 27° C. Normal saline was then added to bring the mixture to a final volume of 5 ml and it was infused I.V. at a rate of 1 ml/minute. The infusions were given 3 to 5 times weekly for a total of 7 to 15 treatments. Shortly after infusions visible tumors became hyperemic and edematous. With repeated infusions objective regressions were observed as indicated below (Table XIII).

TABLE XIII

| Breed | Age | Tumor | Bidimensional Product (cm$^2$) | | |
|---|---|---|---|---|---|
| | | | Pre-TX | Post-TX | % Change |
| Poodle | 11 | Mammary Adenocarcinoma | 17.7 | 10.0 | 44 |
| Boston Terrier | 12 | Mammary Adenocarcinoma | 16.2 | 12.7 | 22 |

TABLE XIII-continued

| Breed | Age | Tumor | Pre-TX | Post-TX | % Change |
|---|---|---|---|---|---|
| | | | Bidimensional Product (cm$^2$) | | |
| Beagle | 7 | Lymphoma | 89.3 | 63.7 | 28 |

The protein A-IgG complexes consisting of 100 μg of protein A plus 25 ml of autologous canine serum were given together with rabbit anti-tumor anti-sera (20 ml) and zymosan activated normal canine serum (Regimen 4, Table XIV) on 2 successive days. The animals were rested on day 3 and then cyclophosphamide and/or adriamycin are given on day 4. This resulted in acute tumoricidal effects in 2 dogs with mammary adenocarcinoma. With repeated administration, 2 dogs showed more than 50% tumor reductions (Table XIV).

TABLE XIV

| Breed | Age (Yrs) | Tumor | PreTX | PostTX | % Change |
|---|---|---|---|---|---|
| | | | Bidimensional Product (cm$^2$) | | |
| Cocker Spaniel | 5 | Mammary Adeno-carcinoma | 18.2 | 8.9 | 56.6 |
| Schnauzer | 8 | Mammary Adeno-carcinoma | 15.3 | 6.1 | 60.9 |

In Vivo Effects of Protein A-IgG Conjugates Prepared From Normal Canine Sera Having ascertained from physicio-chemical studies of PACC effluent that protein A-IgG conjugates were emerging, we sought to test the effectiveness of the conjugates in dogs with various spontaneous canine tumors. Five dogs with various spontaneous tumors were given protein A-IgG complexes. The dosage of PA-IgG employed was developed from studies of the quantity of PA-IgG which would induce visible morphologic changes in the tumor and the ratio of PA of IgG was developed from in vitro studies in which a 1:100 ratio of PA:IgG resulted in optimum release of myeloperoxidase and cathepsins from canine neutrophils. These were prepared by incubating protein A (5 ug/lb) with normal canine serum (0.1 ml/lb) for 60 minutes at 37° C. Normal saline was then added to bring the mixture to a final volume of 10–15 ml and it was infused I.V. at a rate of 1 ml/minute. Infusions were given 2–4 times weekly for a total of 7–16 treatments. Soon after infusions, tumors became hyperemic and edematous. With repeated infusions, objective tumor regressions were observed, as shown in Table XV. In some instances, a subtherapeutic dose of chemotherapy was added to the infusion regimen after the tumor showed inflammatory changes induced by PA-IgG infusions. Under these conditions, tumor regressions were also observed, as shown in Table XVI.

Accordingly, one aspect of the present invention is the method of treating a host having cancer by administering a tumoricidal dose of a preparation which binds to Fc receptor of Fc bearing leukocytes thereby causing release of at least one cytotoxic material from the leukocytes.

TABLE XV
STUDIES OF PROTEIN A-IgG CONJUGATES

| Dog #1 | Tumor | # of Treatments | Pre | Post | % Change |
|---|---|---|---|---|---|
| | | | Bidimensional Product Cm$^2$ | | |
| 1 | Hemangiosarcoma | 13 | 96 | 46 | 51.0 |
| 2 | Mammary Adenocarcinoma | 7 | 16.2 | 11.8 | 57.2 |
| 3 | Lymphoma | 10 | 160.0 | 60.0 | 62.0 |
| 4 | Mammary Adenocarcinoma | 16 | 45.3 | 30.3 | 33.1 |
| 5 | Lymphoma | 11 | 93.6 | 63.7 | 31.9 |

TABLE XVI
STUDIES OF PROTEIN A-IgG CONJUGATES PLUS LOW DOSE CHEMOTHERAPY

| Dog # | Tumor | # of Treatments | Pre | Post | % Change |
|---|---|---|---|---|---|
| | | | Bidimensional Product Cm$^2$ | | |
| 1 | Hemangiosarcoma* | 12 | 86.0 | 4.0 | 96.0 |
| 2 | Squamous Cell Carcinoma* | 15 | 60.0 | 10.0 | 86.0 |
| 3 | Mast Cell Tumor** | 8 | 97.0 | 47.0 | 51.0 |

*Given adriamycin 25 mg/m$^2$ per 1 dose after 12 treatments.
**Given BcNu 1.7 mg/m$^2$ per 1 dose after 5 treatments.

TOXICITY STUDIES WITH PROTEIN A-IgG CONJUGATES IN NORMAL DOGS

A model was developed in the dog to study the toxic effects of conjugates derived from incubating free protein A with canine plasma and to correlate these findings with those observed and previously described in our human studies. In these studies, it was attempted to characterize the pathophysiology of this reaction, examine serologic mediators, study effects of pharmacologic blockade and other methods of attenuating the response and finally draw comparisons with the human reaction.

Four groups were studied. Group 1 was given protein A-IgG conjugates over a 3 minute period. Group 2 was given protein A-IgG conjugates over a 30 minute period. Group 3 were granulocyte depleted dogs given the same regimens as Group 2. Group 4 was given histamine blockade medication before receiving the same regimen as Group 2.

The following parameters were studied:
(a) Left ventricular DP/DT
(b) Cardiac segment length-contractility
(c) Mean aortic blood pressure
(d) Peak left ventricular systolic blood pressure
(e) circumflex coronary artery flow
(f) renal artery flow
(g) femoral artery flow
(h) pulmonary artery flow Results have shown that with rapid infusion of protein A-IgG conjugates, all of the above parameters rapidly delined with a slow return to baseline. With slower infusion of protein A-IgG complexes, there was again reduction in all parameters peaking at 15 minutes, sustained for 45–60 minutes and returning to baseline. The major initial manifestation appeared to be a reduction in left ventricular DP/DT and segment length with secondary effects on mean aortic blood pressure. Granulocyte depletion in dogs receiving the same regimen as Group 2 resulted in a diminution of the cardiovascular effects observed. Use of histamine blockade had little effect in attenuating the cardiovascular responses.

Examination of pathology of various tissues after infusion showed that most striking changes appear to be in the lung with alveolar edema and cellular extravasation into the alveolar space.

In these studies, the dog demonstrates a different pattern of cardiovascular toxicity than we observed in man. The decline in blood flow in the major vessels appears to be due to a reduction in cardiac contractility whereas studies in man under acute conditions showed an increase in cardiac output with reduction in systemic vascular resistance as the cause of the hypotension. In both there is evidence of changes in vascular permeability.

TABLE XVII

Effect of Protein A on Hemolytic Whole Complement Activity[a]

| | C'H$_{50}$ Units (% Reduction) | | | |
|---|---|---|---|---|
| | Human Serum | | | |
| Treatment | H.S. | A.W. | P.M. | Dog Serum |
| Buffer | 240 | 222 | 240 | 128 |
| Protein A (μg/ml)[b] | | | | |
| 3[c] | 104(57) | 151(32) | 191(20) | <10(>92) |
| 78[d] | 80(67) | 133(40) | 135(44) | <10(>92) |
| 2500[c] | 126(48) | 138(38) | 130(46) | <10(>92) |
| Insoluble complexes from: | | | | |
| Autologous serum | 144(40) | 88(60) | 109(55) | <10(>92) |
| Heterologous serum | <10(>96) | <10(>96) | <10(>96) | <10(>92) |
| Homologous IgG | 150(38) | <10(>95) | <10(>96) | <10(>92) |
| Heterologous IgG | <10(>96) | <10(>95) | <10(>96) | <10(>92) |
| C3 deficient homologous serum | 96(60) | 52(77) | 92(62) | <10(>92) |
| Soluble complexes from C3 deficient homologous serum (2500 μg/ml protein A) | 164(32) | 158(29) | 167(30) | <10(>92) |

[a] Determined against sheep erythrocytes sensitized with rabbit IgM hemolysion.
[b] Final concentration in incubation mixture.
[c] Soluble complexes.
[d] Insoluble complexes (equivalence point in precipitin curve).

TABLE XVIII

Levels of C3a and C5a Anaphylatoxins in Serum[a]

| | Subject | | | | | |
|---|---|---|---|---|---|---|
| | H.S. | | A.W. | | P.M. | |
| Serum Treated with: | C3a (ug/ml) | C5a (ug/ml) | C3a (ug/ml) | C5a (ug/ml) | C3a (ug/ml) | C5a (ug/ml) |
| — | 0.620 | 0.048 | 0.222 | <0.030[b] | 0.700 | <0.030[b] |
| Protein A (ug/ml)[c] | | | | | | |
| 3[d] | 38.4 | 1.14 | 30.4 | 1.08 | 40.8 | 2.80 |
| 78[e] | 37.6 | 0.75 | 31.2 | 0.67 | 54.0 | 0.84 |
| 2500[d] | 31.6 | 0.64 | 44.0 | 0.78 | 65.5 | 0.64 |
| Insoluble Serum-Protein A Complexes | 37.5 | 1.61 | 43.0 | 2.40 | 48.3 | 2.24 |
| Insoluble IgG Protein A Complexes | 42.0 | 2.53 | 25.3 | 1.84 | 65.0 | 3.94 |
| Collodion Charcoal | — | <0.030[b] | 0.510 | <0.030[b] | 0.810 | 0.038 |

[a] Average of duplicate determinations, which differed by <8%.
[b] <10% Inhibition of radioimmunoassay.
[c] Final concentration in incubation mixture.
[d] Soluble complexes.
[e] Insoluble complexes (equivalence point in precipitin curve).

Table XVII gives data for the effect of protein A on hemolytic whole complement activity and Table XVIII gives data for C3a and C5a generation from synthetic complexes.

Preferred Embodiment: Product 4 (Acidified Tumor Bearing Sera)

Autologous sera or plasma from tumor bearing hosts, 4 ml/lb, is acidified to pH 2.5 by dropwise addition of 1ON HCl and held for 5 minutes at 27° C. The serum is then rapidly neutralized to pH 7.4 by addition of 1ON NaOH and centrifuged at 1500×g for 30 minutes at 4° C. The supernatant serum is then removed and given I.V. at a rate of 1 ml/minute.

Changes in the major constituents of human plasma after acidification and rapid neutralization by the above procedure are shown below in Table XVIIIA. It may be seen that there is a reduction in total protein and globulin fraction as well as in fibrinogen while other parameters remain essentially unchanged. Table XVIIIB shows reductions in human immunoglobulins G, M and A after treatment of plasma with acid.

TABLE XVIIIA

CHANGES IN HUMAN PLASMA CONSTITUENTS AFTER ACIDIFICATION*

| Parameter | Units | Before | After |
|---|---|---|---|
| Blood urea nitrogen | mg/dl | 17.0 | 14 |
| Creatinine | mg/dl | 1.4 | 1.3 |
| Glucose | mg/dl | 380 | 331 |
| Triglycerides | mg/dl | 130 | 137 |
| Uric acid | mg/dl | 94 | 90 |
| Calcium | mg/dl | 5.7 | 5.2 |
| Phosphorus | mg/dl | 7.6 | 6.1 |

TABLE XVIIIA-continued
CHANGES IN HUMAN PLASMA CONSTITUENTS AFTER ACIDIFICATION*

| Parameter | Units | Before | After |
|---|---|---|---|
| Total protein | g/dl | 10.0 | 8.5 |
| Albumin | g/dl | 5.3 | 4.5 |
| Total bilirubin | mg/dl | 3.8 | 3.8 |
| Alkaline phosphatase | milli IU/ml | 37 | 15 |
| SGOT | milli IU/ml | 8.0 | 15 |
| LDH | milli IU/ml | 132 | 0 |
| K | Meq/L | 3.3 | 2.9 |
| $CO_2$ | Meq/L | 16.5 | 8.5 |
| Prothrombin time | sec | 11.1 | infinity |
| Fibrinogen | Mg/dl | 265 | undetectable |
| Thrombin time | sec | 14 | 50 |
| Partial thromboplastin time | sec | 34 | 150 |

*Human plasma was treated by addition of 10 N HCl to bring pH to 2.5, held 5 minutes and rapidly neutralized by addition of 10 N NaOH.

TABLE XVIIIB
CHANGES IN HUMAN IMMUNOGLOBULINS AFTER ACIDIFICATION

| Sample | IgG (mg/dl) | IgM (mg/dl) | IgA (mg/dl) |
|---|---|---|---|
| Untreated | 1200 | 100 | 110 |
| Acidified | 860 | 100 | 90 |

Autologous acidified serum from tumor bearing hosts shows a significant increase in tumor associated antibodies as measured by indirect immunofluorescence using each dog's own tumor as substrate (Table XIX).

TABLE XIX
TUMOR ASSOCIATED ANTIBODIES IN SERA OF TUMOR BEARING HOSTS*

| Dog #1 | Disease | Untreated Sera | Acid Treated Sera |
|---|---|---|---|
| 1 | Lymphoma | 10,000 | 20,000 |
| 2 | Lymphoma | 10,000 | 30,000 |
| 3 | Lymphoma | 10,000 | 40,000 |
| 4 | Lymphoma | 10,000 | 20,000 |
| 5 | Hemangiosarcoma | 100 | 50,000 |

*Figures represent end point dilutions which gave positive fluorescence sera against the dog's own tumor substrate.

Changes in tumor associated antibodies in sera of dogs with mammary carcinoma after acidification were tested in a radioimmmunoassay in which a tissue culture line of canine mammary adenocarcinoma was used as the target and $125_I$ protein A as indicator to detect cell bound canine IgG. In 10 sera tested, acidification to pH 2.5 followed by rapid neutralization, resulted in increases in tumor associated binding levels of 120±63% (S.D.) above untreated serum values.

Analysis by Sephadex G-200 chromatography of whole serum from a human with breast adenocarcinoma before and after acidification showed the following: (a) acidified serum showed large increase in void volume protein and a relative depletion of protein in the included fraction compared to untreated serum, (b) tumor associated binding measured by radioimmunoassay showed 948% increase in the included fraction and 134% increase in the void volume fraction compared to untreated serum.

Analysis of acidified whole serum after sucrose density gradient ultracentrifugation showed that Clq binding levels were increased up to 400% in fractions greater than 7S compared to untreated serum. Hence, it appears that acidification of tumor bearing serum results in an increase in tumor associated antibodies and the generation of high molecular weight proteins.

Acidified Serum In Treatment Of Spontaneous Tumors

Autologous acidified sera from tumor bearing dogs is given with zymosan activated normal canine serum on day 1 and again in 24 hours later (day 2). The animal is rested on day 3. On day 4, cyclophosphamide is given I.V. (Regimen 2, Table XVIII). The results of this regimen in 5 dogs are shown in Table XX.

TABLE XX
RESPONSE TO TREATMENTS

| | | | Acidification, Complement Activation, Cyclophosphamide | | |
|---|---|---|---|---|---|
| | | | Bidimensional Product | | |
| Dog # | Breed | Disease | Pre Treatment | Post Treatment | Reduction (%) |
| 1 | Puli | Hemangiosarcoma | 140 | 70 | 50 |
| 2 | Labrador | Hemangiosarcoma | 58 | 32 | 39 |
| 3 | Terrier | Melanoma | 50 | 30 | 40 |
| 4 | Springer Spaniel | Lymphoma | 140 | 50 | 70 |
| 5 | Poodle | Mammary adenocarcinoma | 25 | 125 | 50 |
| 6 | Bloodhound | Lymphoma | 160 | 120 | 25 |

An effective variation which produces very considerable tumoricidal effects is as follows: L-asparaginase and cyclophosphamide are given to the host on day 1 and when maximum regression of the tumor is attained, zymosan activated normal canine serum (100 ml) and pre-treatment autologous plasma (4 ml/lb) which is acidified or alkalinized is given and L-asparaginase and cyclophosphamide are administered on the following day (Regimen 5, Table XXII). Results are given in the following Table XXI.

TABLE XXI

| | | | Bidimensional Product ($cm^2$) | | |
|---|---|---|---|---|---|
| Dog # | Breed | Disease | Pre TX | Post TX | Reduction % |
| 1 | Spaniel | Lymphoma | 140 | 35 | 75 |
| 2 | Beagle | Lymphoma | 120 | 30 | 75 |
| 3 | Poodle | Lymphoma | 70 | 35 | 50 |

Preferred Embodiment: Product 5 (Zymosan Activated Plasma)

The administration of normal canine serum after incubation with zymosan a substance known to activate the complement sequence and generate complement by products has resulted in the following in vivo effects:

(a) vasodilatation and decline in blood pressure and tachycardia.

(b) smooth muscle spasmogenic effects.

These effects may be ascribed in part to complement by-products namely anaphylatoxins C3a and C5a.

To activate complement in whole normal canine serum, zymosan (5 gms) is incubated with serum (100 ml) for 10 minutes at 27° C. The zymosan is then removed by centrifugation at 1500×g for 30 minutes. The complement activated serum is then infused I.V. into the tumor bearing host at a rate of 10 ml/minute.

In various regimens employed for the treatment of spontaneous canine tumors, zymosan activated normal canine plasma has been employed as an additional therapeutic modality. Tumoricidal or tumor regressive effects have occurred when zymosan activated canine plasma has been administered together with (a) tumor immune globulin preparation, (b) protein A-IgG complexes, (c) acidified or alkalinized plasma. Tumoricidal effects or regressions have been noted when L-asparaginase, cyclophosphamide or adriamycin are given shortly after administration of each of these products.

Preferred Embodiment: Protein A

Protein A is a constituent of the cell wall of staphylococcus aureus Cowans I and has a capacity to react with Fc region or immunoglobulins for many mammalian species. When injected into tumor bearing dogs, antitumor activity has been observed. Protein A was infused in dosages of 10-80 ug/kg (Regimen 8, Table XXII). This has resulted in transient tumor reductions of 5-20% in 4 animals while one other showed a tumoricidal response. Two others showed no effect.

Multidimensional Immunotherapy

The use of these products alone, in combination with each other or with various chemotherapeutic agents has resulted in very substantial tumoricidal reactions and tumor regressions in dogs with various spontaneous tumors. The regimens employed to bring about these effects are shown in Table XXII and the use of various products in these regimens and results obtained is described in the preferred embodiments.

While all of the examples herein given are for the spontaneous tumors in dogs, it should be recognized that these tumors represent acknowledged and excellent models of their human counterparts. Therapeutic success in the canine model with the protein collodion charcoal system (17, 19) was recently translated to humans in which objective tumor regressions were obtained in 4 of the first 5 consecutive patients treated (20). Thus the data reported herein in dogs with tumors is expected to be predictive of success when the subject methods and compositions are applied to humans with spontaneous tumors as well.

Although the description of the present invention has been disclosed particularly with regard to the use of acid treatment as the dissociative technique, it should be understood that other equivalent dissociative techniques known in the art as further described above are considered as part of the present invention and may be used, as will readily be understood by one skilled in the art.

REFERENCES

1. Bier, M. In Electrophoresis, (ed. M. Bier), Academic Press, New York, New York, 1959, p. 263.
2. Bier, M. In Membrane Process for Industry, Southern Research Institute, Birmingham, Ala., 1966, p. 218.
3. Bier, M. Sixth Intern. Congress Biochem., New York, 1964.
4. Bier, M., Science 125:1084, 1957.
5. Hanning, K. In Electrophoresis, Vol. II, Academic Press, New York, New York, 1967, p. 423.
6. Bier, M., Brucknew, G. C., and Roy, H. E. Trans. Amer. Soc. Artif. Int. Organs 13:227, 1967.
7. Bier, M., and Mourlek, S. P. In Proc. Third Annual American Water Resources Conference, 1967, p. 524.
8. Bier, M., Bruckner, G. C., Cooper, F. C., and Roy, H. E. Concentration of Bacteriophage by Electrophoresis in Transmission of Viruses by Water Route, New

TABLE XXII

SUMMARY OF TREATMENT REGIMENS

| Treatment Regimen | | Day 1 | Day 2 | Day 4 |
|---|---|---|---|---|
| 1 | (a) | FFE | Acidified or alkalinized effluent (Product 1) plus protein A | L-asparaginase Cyclophosphamide Adriamycin |
| 2 | (a) | C' activated sera (P*5) | C' activated sera | L-asparaginase Cyclophosphamide |
|   | (b) | Acidified or alkalinized plasma | Acidified or alkalinized (P4) plasma | |
| 3 | (a) | C' activated sera (P*5) | C' activated sera | Cyclophosphamide Adriamycin |
|   | (b) | Tumor immune globulin (P2) | Anti-tumor IgG (Cohn Fraction) | |
| 4 | (a) | C' activated sera (P*5) | C' activated sera | Cyclophosphamide or Adriamycin |
|   | (b) | Protein A-IgG complexes (P3) | Protein A-IgG complexes | |
| 5 | (a) | L-asparaginase | Acidified or alkalinized autologous plasma plus C' activated sera (days 2 and 3) | L-asparaginase Cyclophosphamide |
|   | (b) | Cyclophosphamide | | |
| 6 | (a) | Complexes of heterologous anti-tumor IgG plus protein A | Complexes of heterologous anti-tumor IgG plus protein A | L-asparaginase Adriamycin Cyclophosphamide |
|   | (b) | C' activated sera (P*5) | C' activated sera | |
| 7 | (a) | Protein A-IgG complexes (P*3) | Protein A-IgG complexes | L-asparaginase |
|   | (b) | Anti-tumor IgG (heterologous) | Anti-tumor IgG (heterologous) | Cyclophosphamide |
| 8 | (a) | Protein A | | |
| 9 | (a) | Protein A-IgG complexes (P*3) | | |

*Refers to Product

The present invention, therefore, is well suited and adapted to attain the objects and has the advantages and features mentioned as well as others inherent therein.

York, 1967, p. 57.

9. Bier, M. In Symposium on Electrodialysis, Electrochemical Society, Boston, Mass., 1968.
10. Bier, M., Beavers, D. C., Merriman, W. G., Merkel, F. K., Eisenman, B., and Starzl, T. Z. Trans. Amer. Soc. Artif. Int. Organs, Vol. XVI, 1970.
11. Forsgren A., Sjoquist J. J. Immunol. 1966, 97:822.
12. Kronvall G., Frommel D. Immunochem. 1970, 7:124.
13. Kessler, S. W. J. Immunol. 1975, 115:1617.
14. Stalenhem G., Gotze 0., Cooper N. R., Sjoquist J., MullerEberhard, H. J. Immunochem. 1973, 10:501.
15. Vallota, E. H., Muller-Eberhard, H. J. J. Exp. Med. 1973, 137:1109.
16. Stalenham, Castensson, S. FEBS Letters 1974, 14:79.
17. Terman, D. S., Yamamoto, T., Mattioli, M., Cook, G., Tillquist, R., Henry, J., Poser, R., Daskal, Y. J. Immunol. 1980 124:795.
18. Holohan, T., Bowles, C., Deisseroth, A, Proc. Am. Assoc. Cancer Res., Am. Soc. Clin. Oncol. 21:241 abstract.
19. Terman D. S., Yamamoto T., Tillquist R. L., Henry J. F., Cook G. L., Silvers A., Shearer W. T.: Science 1980, 209:1257.
20. Terman D. S., Young Y. B., Shearer W. T., Ayus C., Lehane D., Mattioli C., Espada R., Howell J. F., Yamamoto T., Zaleski H. I., Miller L., Frommer P., Fedlman L., Henry J. F., Tillquist R., Cook G., Daskal Y.: N Engl J Med 1981, 305:1195.
21. Young J. B., Ayus J. C., Miller L. K., Webster R. O., Miller R. R., Terman D. S.: Circulation 1981, 64:325 abstract.
22. Martin, R. R., Crowder, J. G., White A. J., J. Immunol. 99 269, 1967.
23. Gustafsen, G. T., Stalenheim G., Forsgren A., Sjoquist, J., J. Immunol. 100, 530, 1968.
24. Heczko, P. B., Grov A., Oeding P., Acta Pathol. Microbiol. Scand. Section B, 81, 731, 1973.
25. Gustafsen, G. T., Sjoquist J., Stalenheim, G., J. Immunol. 98, 1178, 1967.
26. Masuda, S. and Kondo I., Microbiol. Immunol. 23, 1223, 1979.
27. Kronvall, G. and Gewurz, Clin. Exp. Immunol. 7, 211, 1970.
28. Stalenhemin, G., Acta. Pathol. Microbiol. Scand. Section B, 79, 665, 1971.
29. Sjoquist, J. and Stalenheim, G., J. Immunol. 103, 467 1969.
30. Stalenheim, G., Gotze O., Cooper N., Sjoquist J., Muller-Eberhard H., Immunochemistry, 10, 501, 1973.
31. Stalenheim G., Malmheden-Ericksson, I., FEBS Lett. 14 82, 1971.
32. Stalenheim G. and Castensson S., FEBS Lett. 14, 79, 1971.
33. Langone, J. J., In Methods in Enzymology, Academic Press, Inc. N.Y., 70, 356, 1980.
34. Langone, J. J., J. Immunol. Methods. 34, 93, 1980c.
35. Langone, J. J., Boyle, M. D. P, Borsos, T., J. Immunol. 121, 333, 1978.
36. Lancet D., Isenman D., Sjodahl J., Sjoquist J., Pecht I., Biochem. Biophys. Res. Commun. 85, 608, 1978.
37. Hallgren, R. and Stalenheim, Immunology, 30, 755, 1976.
38. Hallgren, R. and Stalenheim G., Immunology 35, 13, 1978.
39. Martin R. R. and White A, J. Immunol. 102, 437, 1969.
40. Campbell D. S., Luescher E., and Lerman L. S., Natl. Acad. Sciences 37:575, 1951.
41. Sjogren H. O., Hellstrom I., Bansal S. C., and Hellstrom K. E., Proc. Natl. Acad. Sciences 68:1372, 1971.
42. Faldt R., Ankerst J., Int. J. Cancer 26:309, 1980.
43. Dorsett, Ioachim, Stolback, Int. J. Cancer 16:779, 1975.
44. Kabat, E. A., Mayer, M. M., Experimental Immunochemistry C. C., Thomas, Springfield, IL, 1948, p. 480.
45. Behring; Kitasato, Dtsch. Med. Wochenschr. 16:1113, 1890.
46. McKhann, C. F.; J. Infect. Dis. 52:268, 1933.
47. McKhann, C. F., Green, A. A.; Coady, H. J. Pediatr. 6:603, 1935.
48. Eley, R. C.; Green, A. A.; McKhann, C. F., J. Pediatr. 8:135, 1936.
49. Stokes, J., Jr., Maris, E. P.; Gellis, S. S., J. Clin. Invest. 23:531, 1944.
50. Ordman, C. W.; Jenning, C. G., Jr.; Janeway, C. A., J. Clin. Invest. 23:541, 1944.
51. Stokes, J.; Neefe, J. R., J.A.M.A. 127:144, 1945.
52. Gellis, S. S.; Stokes, J., Jr.; Brother, G. M.; Hall, W. M.; Gilmore, H. R.; Beyer, E.; Morrissey, R. A., J.A.M.A. 128:1062, 1945.
53. Bruton, O. C., Pediatrics 9:722, 1952.
54. Eibl, M., In Immunoglobulins: Characteristics and Uses of Intravenous Preparations (eds. B. M. Alving, J. S. Finalyson), U.S. Department of Health, and Human Services, pp. 23, 1979.
55. Ochs, H. D., In Immunoglobulins: Characteristics and Uses of Intravenous Preparations (eds. B. M. Alving, J. S. Finalyson), U.S. Department of Health, and Human Services, pp. 9, 1979.
56. Condie, R. M., In Immunoglobulins: Characteristics and Uses of Intravenous Preparations (eds. B. M. Alving, J. S. Finalyson), U.S. Department of Health, and Human Services, pp. 179, 1979.
57. Skvaril, F., Barandun, S., In Immunoglobulins: Characteristics and Uses of Intravenous Preparations (eds. B. M. Alving, J. S. Finalyson), U.S. Department of Health, and Human Services, pp. 201, 1979.
58. Seiler, F. R., In Immunoglobulins: Characteristics and Uses of Intravenous Preparations (eds. B. M. Alving, J. S. Finalyson), U.S. Department of Health, and Human Services, pp. 207, 1979.
59. Funakoshi, S., In Immunoglobulins: Characteristics and Uses of Intravenous Preparations (eds. B. M. Alving, J. S. Finalyson), U.S. Department of Health, and Human Services, pp. 219, 1979.
60. Lindstrom, G. A., Acta Med. Scand. Suppl. 22, 1, 1927.
61. de Carvalho, S., Cancer, 16, 306, 1963.
62. Sekla, B., Holeckova, E., Janele, J., Libansky, J., Hnevkovsky, O., Neoplasma 14, 641, 1967.
63. Tsirimbas, A. D., Pichlmayr, R., Horninung, B., Pfisterer, H., Thierfelder, S., Brendel, W., and Stitch, W., Klin Wschr. 46, 583, 1968.
64. Marsh, B., Flynn, L. and Enneking, W., J. Bone and Joint Surgery 54A, 1367, 1972.
65. Parks, L. C., Smith, W. J., Beebe, B., Winn, L., Rafajko, R., Rolley, R., and Williams G., Melville, Proc. Amer. Cancer Res. and Amer. Soc. Clin. Oncology 16, 134, 1975.
66. Laszlo, J., Buckley, C. E., and Amos, D. B., Blood, 31, 104, 1968.
67. Djerassi, I., Clinical Pediatrics 7, 272, 1968.

68. Herberman, R. B., Oren, M. E., Rogentine, G. N., and Fahey, J. L., Cancer 28, 365, 1971.
69. Brittingham, T. E., and Chaplin, H., Cancer 13,412 1960.
70. Skurkovich, S. V., Kisljak, N. S., Machonkova, L. A., and Begunenko, S. A., Nature 223, 509 1969.
71. Skurkovich, S. V., Makhaonova, L. A., Reznichenko, F. M., and Chervonskiy, G. I., Blood 33, 186, 1969.
72. Ngu, V., Brit. Med. J. 1, 345, 1967.
73. Ghose, T., and Nigam, S. P., Cancer 29, 1398, 1972.
74. Levy, R., Hurwitz, E., Maron, R., and Sela, M., Cancer Res. 35, 1182, 1975.
75. Vial, A. B., and Callahan, W., Cancer 10, 999, 1957.
76. Moolton, F. L., and Cooperband, S. R., Science, 169, 68 1970.
77. Parker, C. W., Pharmacol. Rev. 25, 325, 1973.
78. Segerling, M., Ohanian, S. H., and Borsos, T., Cancer Res. 35, 3195, 1975.
79. Ruddy S., Gigli I., Austen K. F.: N. Engl J Med 287:489, 545,592,642, 1972.
80. Wilson M. R., Arroyaye C. M., Nakamura R. M., Vaughn J. H., Tan E. M.: Clin Exp Immunol 26:11, 1976.
81. Verhaeqen H., DeCock W., DeCree J., Verbruggen F.: Cancer 38:1608, 1976.
82. Ryan G. B., Majno G.: Am J Pathol 86:183, 1977.
83. Hugli T. E., Muller-Eberhard H. J.: "Advances of Immunology," 26. New York: Academic Press, 1978, pp. 1.
84. Cochrane C. G., Muller-Ebarhard H. J.: J. Exp Med 127:371, 1968.
85. Lepow I. H., Willm-Kretschmer K., Patrick R. A., Rosen R. S., Am J Pathol 61:13, 1970.
86. Vallota E. H., Muller-Eberhard H. J.: J Exp Med 137:1109, 1973.
87. Johnson A. R., Hugli T. E., Muller-Eberhard H. J.: Immunology 28:1067, 1975.
88. Hugli T. E.: "The Chemistry and Phsyiology of Human Plasma Proteins." New York: Pergamon Press, 1979 pp. 225.
89. Bokisch V. A., Muller-Eberhard H. J.: J Clin Invest 49:2427, 1970.
90. Chenoweth D. E., Hugli T. E.: J Immunol 124:1517, 1980.
91. Hugli T. E.: J Biol Chem 250:8293, 1975.
92. Fernandez H. N., Hugli T. E.: J Biol Chem 253:6955, 1978.
93. Kassel, R. L., Old, L. J., Carswell, E. A., Fire, N. C., Hardy, W. D., J. Exp. Med. 138, 925, 1973.
94. Cohn E. J., J. Amer Chem Soc 68:459, 1946.
95. Kistler P. and Nitschmann H. S., Vox Sang 7:414, 1962.
96. Killingsworth, L. M. and J. Savoy, 1972 Manual nephelometric methods for immunochemical determination of immunoglobulins IgG, IgA and IgM in human serum Clin Chem 18:335.
97. Mancini, G., A. O. Carbonara and J. F. Heremans, 1965 Immunochemical quantitation of antigens by single radial immunodiffusion. Immunochem. 2:235.
98. Romer, J., A. Gardi and P. Kistler, 1979 Assay of anticomplementary activity in solutions of immunoglobulins. Develop. Biol. Standard 44:147.
99. Laemmli, U. K. 1970 Cleavage of structural proteins during assembly of the head of backteriophage T4. Nature 232:52.
100. Ishiyama, H., K. Okuyama, K. Masuda and J. Yasuda, 1978 Effects of human immunoglobulin preparations on Fc rosette formation between anti D coated erythrocytes and lymphocytes. Z. Immun.-Forsch 154:387.
101. Webster, R. O. and P. M. Henson 1978 Rapid micromeasurement of neutrophil exocytosis. Inflammation 3:129.
102. Anderson, D. C., M. S. Edwards and C. L. Baker 1980 Luminolenhanced chemiluminescence for evaluation of type III group B streptococcal opsonins in human sera. J. Infect. Dis. 141:370.
103. Johnston, R. B., Jr., J. E. Lehmeyer and L. A. Guthrie, 1976 Generation of superoxide anion and chemiluminescence by human monocytes during phagocytosis in contact with surface bound immunoglobulin G. J. Exp. Med. 143:1551.
104. Levy P. C., Shaw, G. M., and LoBuglio A. F., J. Immunol. Vol. 123, No. 2, 594, 1979.
105. Koren, H. S. and Williams M. S., J. Immunol. Vol. 121, No. 5, 1956, 1978.

What is claimed is:

1. A complex of protein A-IgG having the following properties,
   (a) comprises predominantly IgG heavy and light chains and protein A by polyacrylamide gel electrophoresis,
   (b) is identified in heavy sedimenting 7S or >7S fractions on sucrose density gradient with increased Clq binding activity,
   (c) dissociates into lower molecular weight Clq binding fragments under acid conditions,
   (d) is precipitable with 5% polyethylene glycol or other imunoglobulin precipating procedures known to those skilled in the art,
   (e) has anti-complementary activity,
   (f) inhibits Fc dependent lymphocyte rosette formation,
   (g) induces neutrophils to aggregate and release myeloperoxidase, cathepsins and superoxide anions,
   (h) induces hemagglutination of canine erythrocytes,
   (i) induces complement activation with generation of anaphylatoxins,
   (j) induces non-specific complement dependent cytotoxicity of canine mammary adenocarcinoma cells, murine L cells and human erythrocytes, and
   (k) is generated by interaction of plasma with either free or non-covalently bound protein A by complement independent mechanism and is not present in pretreatment serum.

2. A complex of protein A-IgG having the following properties,
   (a) comprises predominantly IgG heavy and light chains and protein A by polyacrylamide gel electrophoresis,
   (b) is identified in heavy sedimenting 7S or >7S fractions on sucrose density gradient with increased Clq binding activity,
   (c) dissociates into lower molecular weight Clq binding fragments under acid conditions,
   (d) is precipitable with 5% polyethylene glycol or other procedures for precipitating immunoglobulins known to those skilled in the art,
   (e) has anti-complementary activity,
   (f) inhibits Fc dependent lymphocyte rosette formation,
   (g) induces neutrophils to release myeloperoxidase, cathepsins and superoxide anions,
   (h) induces hemagglutination of canine erythrocytes, (i) contains antibodies which retain their antigen affinity and have relatively increased cytotoxic capabilitites in the presence of complement, and (j) when infused into tumor bearing hosts at various molar ratios of protein A-IgG complexes results in tumoricidal reactions and tumor regressions.

3. A method of producing the complex of claim 1 comprising, isolating the protein A-IgG complex from one of tumor bearing and normal plasma after perfusion over immobilized staphylococcus aureus protein A by precipitating the protein A-IgG complex from the perfused plasma.

4. A method of producing the complex of claim 2 comprising,
incubating protein A with IgG.

5. A method of producing the complex of claim 1 comprising, incubating protein A with IgG, and
isolating the resulting protein A-IgG complex.

6. The method of claim 5 wherein,
the IgG has tumor specificity.

7. The complex of claim 1 where,
the protein A used in preparing the protein A-IgG preparation includes staphylococcal enterotoxins.

8. The complex of claim 1 where,
the protein A used in preparing the protein A-IgG complex includes staphylococcal enterotoxins A, B, C, E, and F.

* * * * *